US009650892B2

(12) United States Patent
Indo et al.

(10) Patent No.: US 9,650,892 B2
(45) Date of Patent: May 16, 2017

(54) BLENDED MAPPING FOR ESTIMATING FLUID COMPOSITION FROM OPTICAL SPECTRA

(71) Applicant: Schlumberger Technology Corporation, Sugar Land, TX (US)

(72) Inventors: Kentaro Indo, Sugar Land, TX (US); Kai Hsu, Sugar Land, TX (US); Julian J. Pop, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 329 days.

(21) Appl. No.: 14/574,376

(22) Filed: Dec. 17, 2014

(65) Prior Publication Data
US 2016/0177715 A1 Jun. 23, 2016

(51) Int. Cl.
*E21B 47/12* (2012.01)
*E21B 49/08* (2006.01)
*G01V 8/02* (2006.01)
*E21B 49/10* (2006.01)
*G01N 33/24* (2006.01)

(52) U.S. Cl.
CPC ........... *E21B 49/087* (2013.01); *E21B 49/10* (2013.01); *G01N 33/24* (2013.01)

(58) Field of Classification Search
CPC ...... E21B 47/123; E21B 49/08; E21B 49/088; G01V 8/02; G01V 8/10
USPC ............... 166/250.01, 250.16, 264; 356/436; 73/152.42; 703/10; 702/6, 13
See application file for complete search history.

(56) References Cited

U.S. PATENT DOCUMENTS

| 6,350,986 | B1 | 2/2002 | Mullins et al. |
| 7,309,983 | B2 * | 12/2007 | Freedman ............. G01V 11/00 324/303 |
| 7,336,356 | B2 | 2/2008 | Vannuffelen et al. |
| 7,379,180 | B2 | 5/2008 | Vannuffelen et al. |
| 7,428,925 | B2 | 9/2008 | Brown et al. |
| 7,644,610 | B2 | 1/2010 | Meister |

(Continued)

FOREIGN PATENT DOCUMENTS

WO   2012108886 A1   8/2012

OTHER PUBLICATIONS

Dong et al. "New Downhole-Fluid-Analysis Tool for Improved Reservoir Characterization," Society of Petroleum Engineers, SPE 108566, presented at Offshore Europe, Aberdeen, Sep. 4-7, 2008, pp. 1107-1116.

(Continued)

*Primary Examiner* — Kenneth L Thompson

(57) ABSTRACT

Optical spectral data associated with a formation fluid flowing through a downhole formation fluid sampling apparatus is obtained. Based on the obtained optical spectra data, a plurality of measures each relating the formation fluid to a corresponding one of a plurality of different fluid types are estimated. Blending coefficients each corresponding to a different one of the different fluid types are determined and utilized with the predetermined mapping matrices, each corresponding to a different one of the different fluid types, to obtain a blended mapping matrix. A parameter of the formation fluid is then predicted based on a projection of the obtained spectral data onto the blended mapping matrix.

20 Claims, 9 Drawing Sheets

(56) References Cited

U.S. PATENT DOCUMENTS

| | | | |
|---|---|---|---|
| 7,711,488 B2* | 5/2010 | Hsu | E21B 49/10 |
| | | | 702/11 |
| 7,996,153 B2 | 8/2011 | Niemeyer et al. | |
| 8,024,125 B2 | 9/2011 | Hsu et al. | |
| 8,068,226 B2 | 11/2011 | Csutak | |
| 8,146,415 B2 | 4/2012 | Cartellieri | |
| 8,794,318 B2* | 8/2014 | Harrigan | E21B 49/008 |
| | | | 166/100 |
| 9,453,408 B2* | 9/2016 | Indo | E21B 47/102 |
| 2003/0062472 A1 | 4/2003 | Mullins et al. | |
| 2004/0233446 A1 | 11/2004 | Dong et al. | |
| 2005/0216196 A1* | 9/2005 | Akkurt | G01N 24/081 |
| | | | 702/6 |
| 2006/0155474 A1 | 7/2006 | Venkataramanan et al. | |
| 2007/0119244 A1* | 5/2007 | Goodwin | E21B 47/10 |
| | | | 73/152.28 |
| 2011/0048700 A1 | 3/2011 | van Zuilekom et al. | |
| 2011/0087459 A1 | 4/2011 | Zazovsky et al. | |
| 2011/0218736 A1 | 9/2011 | Pelletier | |
| 2012/0018152 A1 | 1/2012 | Zuilekom et al. | |
| 2013/0312956 A1* | 11/2013 | Weston | G01N 21/3577 |
| | | | 166/248 |
| 2014/0096955 A1 | 4/2014 | Indo et al. | |
| 2014/0110105 A1* | 4/2014 | Jones | E21B 47/10 |
| | | | 166/250.01 |

OTHER PUBLICATIONS

Fujisawa, et al. "Analyzing Reservoir Fluid Composition In-Situ in Real Time: Case Study in a Carbonate Reservoir," Society of Petroleum Engineers, SPE 84092, presented at the SPE Annual Technical Conference and Exhibition held in Denver, Colorado, U.S.A., Oct. 5-8, 2003, pp. 1-9.

Indo, et al. "Estimation of Fluid Composition from Downhole Optical Spectrometry," SPE 166464-MS, SPE Annual Technical Conference and Exhibition held in New Orleans, Louisiana, USA, Sep. 30-Oct. 2, 2013, pp. 1-21.

International Search Report and Written Opinion issued in PCT/US2013063072 on Jan. 1, 2014, 11 pages.

Venkataramanan, et al. "Downhole Fluid Analysis and Fluid Comparison Algorithm as an Aid to Reservoir Characterization," Society of Petroleum Engineers, SPE 100937, presented at the 2006 SPE Asia Pacific Oil & Gas Conference and Exhibition held in Adelaide, Australia, Sep. 11-13, 2006, pp. 1-16.

* cited by examiner

BLENDED MAPPING FOR ESTIMATING FLUID COMPOSITION FROM OPTICAL SPECTRA

BACKGROUND OF THE DISCLOSURE

Downhole fluid analysis (DFA) is often used to provide information in real time about the composition of subterranean formations or reservoir fluids. Such real-time information can be utilized to improve or optimize the effectiveness of formation testing tools during a sampling processes in a given well, including sampling processes which don't return a captured formation fluid sample to the Earth's surface. For example, DFA permits reducing and/or optimizing the number of samples captured and brought back to the surface for further analysis. Some known DFA tools such as the Live Fluid Analyzer (LFA), the Composition Fluid Analyzer (CFA), and the In-situ Fluid Analyzer, each commercially available from Schlumberger Technology Corporation, can measure absorption spectra of formation fluids under downhole conditions. Such fluid analyzers provide ten (LFA, CFA) or 36 (IFA) channels, each of which corresponds to a different wavelength of light that corresponds to a measured spectrum ranging from visible to near infrared wavelengths. The output of each channel represents an optical density (i.e., the logarithm of the ratio of incident light intensity to transmitted light intensity), where an optical density (OD) of zero (0) corresponds to 100% light transmission, and an OD of one (1) corresponds to 10% light transmission. The combined OD output of the channels provides spectral information that can be used to determine the composition and various other parameters of formation fluids.

SUMMARY OF THE DISCLOSURE

This summary is provided to introduce a selection of concepts that are further described below in the detailed description. This summary is not intended to identify indispensable features of the claimed subject matter, nor is it intended for use as an aid in limiting the scope of the claimed subject matter.

The present disclosure introduces a method that includes obtaining in-situ optical spectral data associated with a formation fluid flowing through a downhole formation fluid sampling apparatus. Based on the obtained optical spectra data, measures, each relating the formation fluid to a corresponding one of a plurality of different fluid types, are estimated. Based on the measures, blending coefficients, each corresponding to a different one of the different fluid types, are obtained. A blended mapping matrix is then obtained utilizing the blending coefficients and predetermined mapping matrices each corresponding to a different one of the different fluid types. The method also includes predicting a parameter of the formation fluid flowing through the downhole formation fluid sampling apparatus based on a projection of the obtained spectral data onto the blended mapping matrix.

The present disclosure also introduces an apparatus that includes a downhole formation fluid sampling apparatus operable within a wellbore extending from a wellsite surface into a subterranean formation, and surface equipment disposed at the wellsite surface and in communication with the downhole formation fluid sampling apparatus. The downhole formation fluid sampling apparatus and the surface equipment are collectively operable to obtain in-situ optical spectral data associated with a formation fluid flowing through the downhole formation fluid sampling apparatus, and then estimate, based on the obtained optical spectra data, measures each relating the formation fluid to a corresponding one of different fluid types. The downhole formation fluid sampling apparatus and the surface equipment are also collectively operable to determine, based on the measures, blending coefficients each corresponding to a different one of the different fluid types, and obtain a blended mapping matrix utilizing the blending coefficients and predetermined mapping matrices each corresponding to a different one of the different fluid types. The downhole formation fluid sampling apparatus and the surface equipment are also collectively operable to predict a parameter of the formation fluid flowing through the downhole formation fluid sampling apparatus based on a projection of the obtained spectral data onto the blended mapping matrix.

These and additional aspects of the present disclosure are set forth in the description that follows, and/or may be learned by a person having ordinary skill in the art by reading the materials herein and/or practicing the principles described herein. At least some aspects of the present disclosure may be achieved via means recited in the attached claims.

BRIEF DESCRIPTION OF THE DRAWINGS

The present disclosure is understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
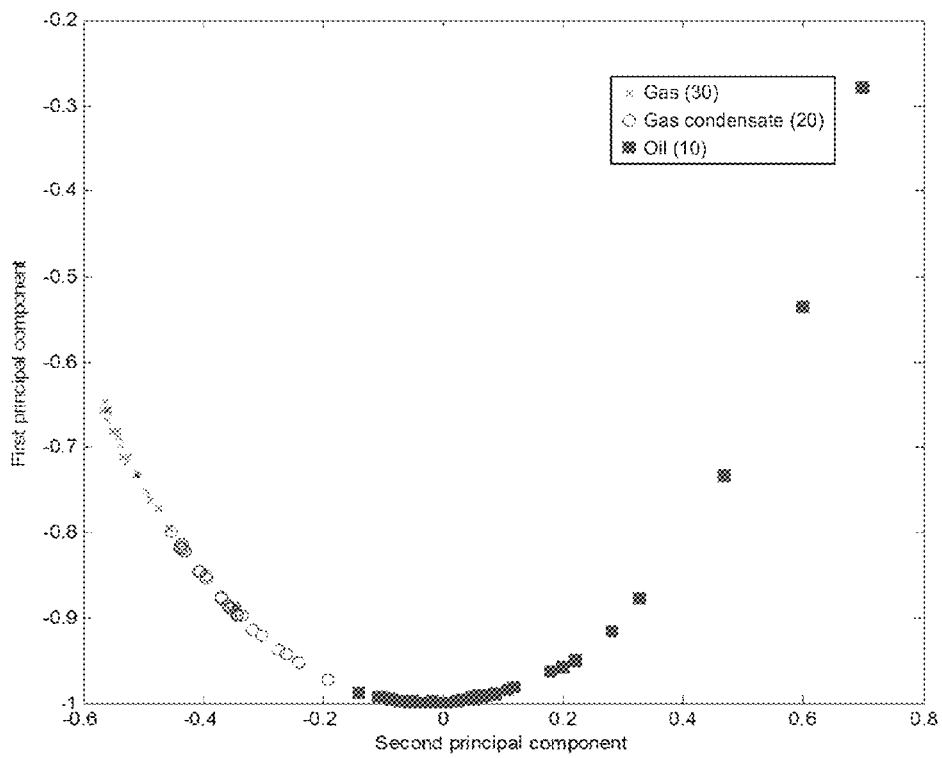
FIG. 1 is a graph depicting one or more aspects related to the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for simplicity and clarity and does not in itself dictate a relationship between the various embodiments and/or configurations discussed except where specifically noted as indicating a relationship. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

The CFA was one of the first tools utilized for downhole fluid analysis (DFA), performing downhole compositional analysis of hydrocarbon mixtures. Still in use today, the CFA utilizes an optical spectrometer having seven near-infrared (NIR) channels to estimate partial density of the carbon species in gas and gas condensate. The equation of the CFA algorithm is set forth below as Equation (1):

$$y = xB \quad (1)$$

where x denotes CFA optical densities (OD) at seven channels, y denotes estimated partial densities of carbon species, and B is a mapping matrix calibrated against an optical spectra database, such as by utilization of principal component regression (PCR).

More recently developed downhole tools for performing DFA utilize an optical spectrometer having 36 channels. The evolution towards greater numbers of spectrometer channels has given rise to additional methods for estimating various fluid parameters, employing algorithms optimized for oil as well as gas and gas condensate. The present disclosure, however, introduces aspects in the context of a downhole tool having a 20-channel spectrometer. Such aspects are also applicable or readily adaptable for use with DFA employing a 36-channel spectrometer and/or another spectrometer having another number of channels.

According to Beer-Lambert's law, optical density (absorption) is proportional to an absorption coefficient $\alpha$, concentration (or partial density) $\rho$, and optical pathlength $l$, as set forth below in Equation (2):

$$OD(\lambda) = \alpha(\lambda) \cdot \rho \cdot l \quad (2)$$

where $\lambda$ denotes wavelength of an electro-magnetic wave, such as UV-visible-NIR light, mid-IR light, and/or others.

Optical density of multi-component systems can be described as a linear combination of contributions from individual carbon components (e.g., C1, C2, C3, C4, C5, C6+ and CO2) if there is no substantial interaction between components, as set forth below in Equation (3):

$$OD(\lambda) = \sum_i OD_i(\lambda) = OD_{C1}(\lambda) + OD_{C2}(\lambda) + OD_{C3}(\lambda) + OD_{C4}(\lambda) + \quad (3)$$

$$OD_{C5}(\lambda) + OD_{C6+}(\lambda) + OD_{CO2}(\lambda)$$

$$= \alpha_{C1}(\lambda) \cdot \rho_{C1} \cdot l + \alpha_{C2}(\lambda) \cdot \rho_{C2} \cdot l + \alpha_{C3}(\lambda) \cdot \rho_{C3} \cdot l + \alpha_{C4}(\lambda) \cdot$$

$$\rho_{C4} \cdot l + \alpha_{C5}(\lambda) \cdot \rho_{C5} \cdot l + \alpha_{C6+}(\lambda) \cdot \rho_{C6+} \cdot l + \alpha_{CO2}(\lambda) \cdot \rho_{CO2} \cdot l$$

Equation (3) can be normalized and/or otherwise altered to a concentration-independent form as follows. To start, the relationship between weight fraction ($\omega_i$) and concentration (or partial density) may be as set forth below in Equation (4):

$$(\omega_{C1}, \omega_{C2}, \omega_{C3}, \omega_{C4}, \omega_{C5}, \omega_{C6+}, \omega_{CO2}) = \left(\frac{\rho_{C1}}{\rho_{total}}, \frac{\rho_{C2}}{\rho_{total}}, \dots, \frac{\rho_{CO2}}{\rho_{total}}\right) \quad (4)$$

where total density is given by $\rho_{total} = \Sigma_i \rho_i$ ($i$=C1, C2, C3, C4, C5, C6+ and CO2).

Normalizing by weight fraction of a particular component, ($\omega_C$) (C=C1, C2, C3, C4, C5, C6+ or CO2), results in Equation (5) set forth below:

$$\left(\frac{\omega_{C1}}{\omega_C}, \frac{\omega_{C2}}{\omega_C}, \dots, \frac{\omega_{CO2}}{\omega_C}\right) = \left(\frac{\omega_{C1}\rho_{total}}{\omega_C\rho_{total}}, \frac{\omega_{C2}\rho_{total}}{\omega_C\rho_{total}}, \dots, \frac{\omega_{CO2}\rho_{total}}{\omega_C\rho_{total}}\right) = \quad (5)$$

$$\left(\frac{\rho_{C1}}{\rho_C}, \frac{\rho_{C2}}{\rho_C}, \dots, \frac{\rho_{CO2}}{\rho_C}\right)$$

$$= (\bar{\rho}_{C1}, \bar{\rho}_{C2}, \bar{\rho}_{C3}, \bar{\rho}_{C4}, \bar{\rho}_{C5}, \bar{\rho}_{C6+}, \bar{\rho}_{CO2})$$

where $\omega_i \rho_{total} = \rho_i$ and $\bar{\rho}_i = \rho_i/\rho_C$ pertain to the relative concentration of a component C (i=C1, C2, C3, C4, C5, C6+ or CO2).

Equation (3) may also be rearranged if $OD_C(\lambda')$ is non-zero, as set forth below in Equation (6):

$$OD(\lambda) = \sum_i OD_i(\lambda) = OD_C(\lambda') \sum_i \frac{OD_i(\lambda)}{OD_C(\lambda')} \quad (6)$$

$$= OD_C(\lambda') \sum_i \frac{\alpha_i(\lambda) \cdot \rho_i \cdot l}{\alpha_C(\lambda') \cdot \rho_C \cdot l}$$

$$= OD_C(\lambda') \cdot \sum_i \bar{\alpha}_i(\lambda) \cdot \bar{\rho}_i$$

where $\bar{\alpha}_i(\lambda) = \alpha_i(\lambda)/\alpha_C(\lambda')$ is the relative absorption coefficient of $\alpha_i(\lambda)$ to $\alpha_C(\lambda')$, and where $\bar{\rho}_i = \rho_i/\rho_C$ is the relative concentration of $\rho_i$ to $\rho_C$.

Thus, the normalized optical density by optical density of a component C at wavelength $\lambda'$ can be expressed as set forth below in Equation (7):

$$\overline{OD}(\lambda) = \frac{OD(\lambda)}{OD_C(\lambda')} = \sum_i \bar{\alpha}_i(\lambda) \cdot \bar{\rho}_i \quad (7)$$

($i$ = C1, C2, C3, C4, C5, C6+ and CO2)

Equation (7) is temperature, pressure, and pathlength independent because the variation of the absorption coefficient $\bar{\alpha}(\lambda)$ against temperature and pressure is nearly constant. For gas and gas condensate samples, C=C1 and $\lambda'$=1650 nm may be used, resulting in Equation (8) set forth below:

$$\overline{OD}_{gas}(\lambda) = \frac{OD(\lambda)}{OD_{C1}(1650 \text{ nm})} = \bar{\alpha}_{C1}(\lambda) + \bar{\alpha}_{C2}(\lambda) \cdot \bar{\rho}_{C2} + \bar{\alpha}_{C3}(\lambda) \cdot \bar{\rho}_{C3} + \quad (8)$$

$$\bar{\alpha}_{C4}(\lambda) \cdot \bar{\rho}_{C4} + \bar{\alpha}_{C5}(\lambda) \cdot \bar{\rho}_{C5} + \bar{\alpha}_{C6+}(\lambda) \cdot \bar{\rho}_{C6+} + \bar{\alpha}_{CO2}(\lambda) \cdot \bar{\rho}_{CO2}$$

where $\bar{\rho}_{C1} = \rho_{C1}/\rho_C = 1$ and $\bar{\alpha}_i(\lambda) = \alpha_i(\lambda)/\alpha_{C1}(1650 \text{ nm})$.

In a similar way, C=C6+ and $\lambda'$=1725 nm may be used for oil samples, resulting in Equation (9) set forth below:

$$\overline{OD}_{oil}(\lambda) = \quad (9)$$

$$\frac{OD(\lambda)}{OD_{C6+}(1725 \text{ nm})} = \bar{\alpha}_{C1}(\lambda) \cdot \bar{\rho}_{C1} + \bar{\alpha}_{C2}(\lambda) \cdot \bar{\rho}_{C2} + \bar{\alpha}_{C3}(\lambda) \cdot \bar{\rho}_{C3} +$$

$$\bar{\alpha}_{C4}(\lambda) \cdot \bar{\rho}_{C4} + \bar{\alpha}_{C5}(\lambda) \cdot \bar{\rho}_{C5} + \bar{\alpha}_{C6+}(\lambda) + \bar{\alpha}_{CO2}(\lambda) \cdot \bar{\rho}_{CO2}$$

where $\bar{\rho}_{C6+} = \rho_{C6+}/\rho_C = 1$ and $\bar{\alpha}_i(\lambda) = \alpha_i(\lambda)/\alpha_{C6+}(1725 \text{ nm})$.

In Equations (8) and (9), however, $OD_C(\lambda')$ is an unknown variable at this point in the analysis. From Equation (7), however, one can obtain Equation (10) set forth below:

$$OD_C(\lambda') = \frac{OD(\lambda)}{\sum_i \overline{\alpha}_i(\lambda) \cdot \overline{\rho}_i} \quad (10)$$

For gas and gas condensate spectra, $\lambda'=\lambda=1650$ nm may be chosen, and terms of C3, C4, C5, C6+ and CO2 can be truncated from Equation (10) because the contribution from these terms at 1650 nm is negligible, thus resulting in Equation (11) set forth below:

$$OD_{C1}(1650 \text{ nm}) = \frac{OD(1650 \text{ nm})}{1 + \overline{\alpha}_{C2}(1650 \text{ nm}) \cdot \overline{\rho}_{C2}} \quad (11)$$

Likewise for oil spectra, $\lambda'=\lambda=1725$ nm may be chosen, and terms of C1, C2 and CO2 can be truncated, thus resulting in Equation (12) set forth below:

$$OD_{C6+}(1725 \text{ nm}) = \frac{OD(1725 \text{ nm})}{\overline{\alpha}_{C3}(1725 \text{ nm}) \cdot \overline{\rho}_{C3} + \overline{\alpha}_{C4}(1725 \text{ nm}) \cdot \overline{\rho}_{C4} + \overline{\alpha}_{C5}(1725 \text{ nm}) \cdot \overline{\rho}_{C5} + 1} \quad (12)$$

The color spectrum can also be taken into account for oil spectra cases. That is, since there is less vibrational absorption from C1, C2, C3, C4, C5, C6+ and CO2 at 1500 nm, optical density at 1500 nm originates primarily from color (if there is any). Thus, color absorption at 1725 nm can be described as proportional to optical density at 1500 nm, as set forth below in Equation (13):

$$OD_{Color}(1725 \text{ nm}) = \beta \cdot OD(1500 \text{ nm}) \quad (13')$$

Alternatively, the $OD_{Color}(1725 \text{ nm})$ may be expressed as set forth below in Equation (13'):

$$OD_{Color}(1725 \text{ nm}) = \beta e^{(\phi/1725 \text{ nm})} + \gamma \quad (13)$$

where $\beta$, $\phi$ and $\gamma$ are adjustable parameters determined in a manner similar to $\beta$ in equation (13). Moreover, the analysis that follows may be applicable or readily adaptable for instances where Equation (13') is utilized as an alternative to Equation (13).

Combining Equations (12) and (13) results in Equation (14) set forth below:

$$OD_{C6+}(1725 \text{ nm}) = \frac{OD(1725 \text{ nm})}{\overline{\alpha}_{C3}(1725 \text{ nm}) \cdot \overline{\rho}_{C3} + \overline{\alpha}_{C4}(1725 \text{ nm}) \cdot \overline{\rho}_{C4} + \overline{\alpha}_{C5}(1725 \text{ nm}) \cdot \overline{\rho}_{C5} + 1 + \beta \cdot OD(1500 \text{ nm})} \quad (14)$$

Thus, the linear relationship between normalized optical density and relative concentration for gas and gas condensate samples may be as set forth below in Equations (15) and (16):

$$\overline{OD}_{gas}(\lambda) = \frac{OD(\lambda)}{OD_{C1}(1650 \text{ nm})} = \overline{\alpha}_{C1}(\lambda) + \overline{\alpha}_{C2}(\lambda) \cdot \overline{\rho}_{C2} + \overline{\alpha}_{C3}(\lambda) \cdot \overline{\rho}_{C3} + \overline{\alpha}_{C4}(\lambda) \cdot \overline{\rho}_{C4} + \overline{\alpha}_{C5}(\lambda) \cdot \overline{\rho}_{C5} + \overline{\alpha}_{C6+}(\lambda) \cdot \overline{\rho}_{C6+} + \overline{\alpha}_{CO2}(\lambda) \cdot \overline{\rho}_{CO2} \quad (15)$$

$$OD_{C1}(1650 \text{ nm}) = \frac{OD(1650 \text{ nm})}{1 + \overline{\alpha}_{C2}(1650 \text{ nm}) \cdot \overline{\rho}_{C2}} = \frac{1}{\eta_{C1}} \quad (16)$$

Similarly, the linear relationship between normalized optical density and relative concentration for oil samples may be as set forth below in Equations (17) and (18):

$$\overline{OD}_{oil}(\lambda) = \frac{OD(\lambda)}{OD_{C6+}(1725 \text{ nm})} \quad (17)$$
$$= \overline{\alpha}_{C1}(\lambda) \cdot \overline{\rho}_{C1} + \overline{\alpha}_{C2}(\lambda) \cdot \overline{\rho}_{C2} + \overline{\alpha}_{C3}(\lambda) \cdot \overline{\rho}_{C3} + \overline{\alpha}_{C4}(\lambda) \cdot \overline{\rho}_{C4} + \overline{\alpha}_{C5}(\lambda) \cdot \overline{\rho}_{C5} + \overline{\alpha}_{C6+}(\lambda) + \overline{\alpha}_{CO2}(\lambda) \cdot \overline{\rho}_{CO2}$$

$$OD_{C6+}(1725 \text{ nm}) = \frac{OD(1725 \text{ nm})}{\overline{\alpha}_{C3}(1725 \text{ nm}) \cdot \overline{\rho}_{C3} + \overline{\alpha}_{C4}(1725 \text{ nm}) \cdot \overline{\rho}_{C4} + \overline{\alpha}_{C5}(1725 \text{ nm}) \cdot \overline{\rho}_{C5} + 1 + \beta \cdot OD(1500 \text{ nm})} \quad (18)$$
$$= \frac{1}{\eta_{C6+}}$$

where
$$\overline{\rho}_i = \rho_i/\rho_C = \omega_i/\omega_C.$$

These linear relationships may be utilized within a method of mapping matrix calibration according to one or more aspects of the present disclosure, as described below.

Measured optical density is often affected by light scattering and offset due to refractive index contrasts, as well as absorption by the sample in the flowline of the downhole tool. For example, light scattering may be caused by particles (e.g., mud, sand, etc.), bubbles, water droplets, and organic matter (e.g., asphaltenes) that may be suspended in the flowline fluid. Dirty or coated optical windows may also cause light scattering. If the size of the scattering object is much larger than the wavelength of light, then the scattering effect is less wavelength-dependent (geometric scattering). If the size of the scattering object is comparable or smaller than the wavelength of light, then the resulting scattering effects may be more wavelength-dependent (Mie/Rayleigh scattering).

With regard to a refractive index effect, if the spectrometer baseline is calibrated with air in the flowline of the downhole tool, then the zero optical density is defined in the air, with reflectivity at the boundaries between sapphire and air. The reflectivity at the boundaries depends on the refractive index of the fluid in the flowline. This effect appears as being a nearly constant negative offset on a spectrum.

To reduce these scattering and refractive index effects, the measured optical spectra may be aligned (e.g., shifted vertically), and optical density at a predetermined wavelength (e.g., 1600 nm) may be forced to zero. In certain embodiments, methods within the scope of the present disclosure may utilize other forms of pretreating the measured optical spectra.

The DFA and associated methods within the scope of the present disclosure may utilize mapping matrices B that are calibrated separately for gas, gas condensate, and oil. The normalized optical spectra data set resulting from the above analysis may be utilized as a set of calibrants in a partial least squares (PLS) process. There are, however, unknowns in the normalization term, such as $\overline{\alpha}_{C2}(1650 \text{ nm})$ in Equation (16) and $\{\overline{\alpha}_{C3}(1725 \text{ nm}) + \overline{\alpha}_{C4}(1725 \text{ nm}) + \overline{\alpha}_{C5}(1725 \text{ nm})\}$ and $\beta$ in Equation (18). These unknown parameters may be optimized so that a mapping matrix obtained from a PLS calibration may yield minimal composition errors. Errors of compositions (C1, C2, C3, C4, C5, C6+ and CO2) to be minimized by the optimization may be defined as set forth below in Equation (19):

$$e_w = \frac{1}{N}\sqrt{\sum_j \sum_k (w'_{jk} - w_{jk})^2} \quad (19)$$

(k: C1, C2, C3, C4, C5, C6+ and CO2)

where N denotes the number of samples, $w_{jk}$ represents the reference weight fraction of component k for sample j in the set of calibrants, and $w_{jk}'$ represents the predicted weight fraction of component k for sample j.

Laboratory-measured optical spectra employed for the PLS calibration may be converted into equivalent downhole tool channel spectra (by known or future-developed methods), since measurement parameters of the laboratory spectrometer and the downhole tool spectrometer may have substantial differences. For example, the lab-measured data may be converted into equivalent 20-channel spectra. The spectra obtained with the downhole tool spectrometer, however, may also or instead be utilized for the PLS calibration, such that the channel conversion may not be performed. Optical density adjustments may also be made to account for noise and any hardware dependency from unit to unit. Such adjustments, which may include intentionally adding noise, may reduce the weight on error-sensitive channels in constructing the mapping matrices B. Consequently, the mapping may be more robust against effects of the hardware dependency or noise.

The mapping matrices B are calibrated by the mapping set forth below in Equation (20).

$$\begin{Bmatrix} X \\ X+\delta X_1 \\ \vdots \\ X+\delta X_N \end{Bmatrix} B = \begin{Bmatrix} Y \\ Y \\ Y \\ Y \end{Bmatrix} \quad (20)$$

where X is the spectral dataset, $\delta X$ is OD error (e.g., known from knowledge of the instrument), Y is relative concentration of components (e.g., C1, C2, C3, C4, C5, C6+, and CO2), and N is the number of sets of adjusted spectral datasets that may be employed to calibrate the mapping matrix, forcing $X+\delta X$ to be mapped to Y. Here, the mapping matrices B may be determined via PLS. However, other methods are also within the scope of the present disclosure, such as PCR, multiple regression, independent component analysis (ICA), and/or other methods for determining coefficients which map known inputs to known outputs.

As mentioned above, three different mapping matrices may be utilized, such as one each for oil, gas and gas condensate, prior to composition analysis. To identify the fluid types from a spectrum, projections onto loading vectors obtained individually from oil, gas, and gas condensate spectra in the database are performed. For example, the database spectra may be vertically aligned at a predetermined wavelength (e.g., 1600 nm), and channels around the hydrocarbon absorption peaks (e.g., from 1500 nm to 1800 nm) may be used. Each spectrum may then be normalized by summation over available spectral data points (e.g., 1500 nm to 1800 nm), as set forth below in Equation (23):

$$x = (OD - OD(1600 \text{ nm})) / \sum_{\lambda=1500\,nm}^{1800\,nm} |OD(\lambda) - OD(1600 \text{ nm})| \quad (23)$$

where $OD=\{OD(\lambda)\}$ is a vector (spectrum) constructed from the optical densities at the wavelengths $\lambda$.

Loading vectors may then be obtained using, for example, singular value decomposition (SVD), or other forms of principal component analysis (PCA), on the database of each fluid type, as set forth below in Equation (24):

$$X_i = U_i \Lambda_i V_i^T \text{ (i=oil, gas, gas condensate)} \quad (24)$$

where U denotes the scores of X, $\Lambda$ denotes the diagonal matrix of eigenvalues of X, and V denotes loading matrices of X. Projection $p_i$ of a spectrum x onto the loading vector $V_i$ may then be acquired as set forth below in Equation (25):

$$p_i = x \cdot V_i \quad (25)$$

Upon examining normalized eigenvalues of the spectral database of oil, gas, and gas condensate, it is noted that the eigenvalues of the first and second principal components dominate more than 90% of the total eigenvalues/contributions. Thus, the first two components may be deemed imperative to classifying spectra as belonging to a given fluid type. Accordingly, projections onto the first two loading vectors of oil, gas, and gas condensate may be evaluated as set forth below in Equation (26):

$$p_{i1\&2} = \sqrt{p_{i1}^2 + p_{i2}^2} \quad (26)$$

The resulting $p_{i1\&2}$ may then be compared to determine the predominant fluid type. For example, the largest of the resulting $p_{i1\&2}$ may be considered to most closely represent the spectral shape for each of the three fluid types independently.

Once the mapping matrices are obtained, the calibration process described above may no longer be utilized for performing the composition analysis. For the mapping matrix calibration using the PLS regression, the spectra used for the calibration were normalized using Equation (16) or (18). The unknown parameters $(\bar{\alpha}_{C2}, \bar{\alpha}_{C3}, \bar{\alpha}_{C4}, \bar{\alpha}_{C5}, \beta)$ are optimized, and relative concentrations $(\bar{\rho}_{C2}, \bar{\rho}_{C3}, \bar{\rho}_{C4}, \bar{\rho}_{C5})$ in the normalization factor may be obtained from the database that was used for the calibration. Then, composition prediction for an unknown spectrum (x) can be expressed using an unknown normalization factor $\eta$ as set forth below in Equation (27):

$$\eta x \cdot B = \eta (\bar{\rho}_{C1}, \bar{\rho}_{C2}, \bar{\rho}_{C3}, \bar{\rho}_{C4}, \bar{\rho}_{C5}, \bar{\rho}_{C6+}, \bar{\rho}_{CO2})^T \quad (27)$$

The normalization factor $\eta$ may then be disregarded when the weight fraction is calculated from relative concentration, as set forth below in Equation (28):

$$\omega_i = \frac{\eta \bar{\rho}_i}{\eta \sum_i \bar{\rho}_i} = \frac{\bar{\rho}_i}{\bar{\rho}_{C1} + \bar{\rho}_{C2} + \bar{\rho}_{C3} + \bar{\rho}_{C4} + \bar{\rho}_{C5} + \bar{\rho}_{C6+} + \bar{\rho}_{CO2}} \quad (28)$$

One or more aspects described above may, in some implementations, present issues related to fluids near the boundary between two different fluid types, such as the boundary between oil and gas condensate, or the boundary between gas condensate and gas. Moreover, the composition estimation may be inaccurate if a fluid is misclassified, such as if a gas condensate is misclassified as a gas. The composition prediction may also have less than adequate accuracy if the analyzed fluid is near the boundary between fluid types, even if the fluid is not misclassified. Moreover, one or more aspects of the approach described above may, in some implementations, present issues related to the discontinuation of fluid composition and GOR (gas-oil ratio) during a station log, such as when the selected fluid type switches from one to another. However, the present disclosure also introduces a methodology of blending the mapping matrices near the fluid boundaries, which may aid in mitigating such issues.

Such blending results in a single mapping matrix that utilizes a linear combination of the mapping matrices described above. The concept is introduced in Equation (29), set forth below:

$$B = B_0 + \sum_i a_i(B_i - B_{i-1}) \quad (i = 1, 2, \ldots) \tag{29}$$

$B_i$ is a mapping matrix calibrated against a fluid type, i, segmented in the database. The coefficient, $a_i$, is defined using a logistic function, as set forth below in Equation (30):

$$a_i = \frac{1}{1 + \exp(-c_i t + d_i)} \tag{30}$$

where $c_i$ and $d_i$ are coefficients determined by minimizing h for the preexisting database samples, $X=\{x1, x2, \ldots\}$ and $Y=\{y1, y2, \ldots\}$, such as in the example set forth below in Equation (30.1):

$$h = \min_{c_i, d_i} \|XB(t, c_i, d_i) - Y\|^2 \tag{30.1}$$

In Equation (30.1), $x_k$ and $y_k$ denote, respectively, optical spectrum and corresponding relative concentration of the pseudo components in the preexisting database, and t is a measure of fluid type, which is determined from each $x_k$, as described below. The measure of fluid type t may be, for example, an estimation of the percentage (by weight or volume) of each fluid type within the sample obtained downhole. However, other measures t of the fluid types are also within the scope of the present disclosure.

In the example in which the analyzed fluid is selected from oil, gas condensate, and gas, mapping matrices are obtained from three segments: oil (i=0), gas condensate (i=1), and gas (i=2). Thus, Equation (29) may be rewritten as set forth below in Equation (31):

$$B = B_{Oil} + a_1(B_{gascond} - B_{Oil}) + a_2(B_{gas} - B_{gascond}) \tag{31}$$

The mapping matrices for oil, gas condensate, and gas can then be obtained utilizing Equation (31), as set forth below in Equations (32)-(34):

$$B = B_{oil}, \text{ if } a_1 = 0 \text{ and } a_2 = 0 \tag{32}$$

$$B = B_{gascond}, \text{ if } a_1 = 1 \text{ and } a_2 = 0 \tag{33}$$

$$B = B_{gas}, \text{ if } a_1 = 1 \text{ and } a_2 = 1 \tag{34}$$

The measure of fluid types t in Equation (30) is obtained utilizing a projection of optical spectra onto a loading vector that is obtained utilizing PCA on samples in the spectral database. See, for example, the description above with respect to Equations (24) and (25). Spectral features in eight wavelength channels ranging from about 1500 nm to about 1800 nm around hydrocarbon peaks may be utilized for the PCA. However, other numbers of channels and/or other wavelengths may also be utilized. Prior to the projection, the optical spectrum, x, may be shifted using the OD at 1600 nm, and may be normalized (such as to reduce spectral offset and temperature and pressure effects), such as is set forth below in Equation (35):

$$x' = \frac{x - OD(1600 \text{ nm})}{\sqrt{\sum_{\lambda=1500nm}^{1800nm} (OD(\lambda) - OD(1600 \text{ nm}))^2}} \tag{35}$$

The measure of fluid types t in Equation (30) may then be defined as set forth below in Equation (36):

$$t = (x' \cdot v)^3 \tag{36}$$

where v represents the second principal vector of the matrix $V_{oil}$. It is noted that implementations within the scope of the present disclosure may utilize a value other than "3" for the exponent in Equation (36).

FIG. 1 is a graph depicting example projections of optical spectra onto the first (y-axis) and second (x-axis) eigenvectors obtained from approximately 70 example spectra. The example spectra include oil samples (data 10), gas condensate samples (data 20), and gas samples (data 30). The second principal component depicts the example trend of the fluid type, such as gas where the second principal component is less than about −0.45, gas condensate where the second principal component ranges between about −0.45 and about −0.15, and oil where the second principal component is greater than about −0.15. It is noted that FIG. 1 and the data therein are merely examples, and other examples, values, fluid types, and fluid type trends are also within the scope of the present disclosure.

Figure 2:
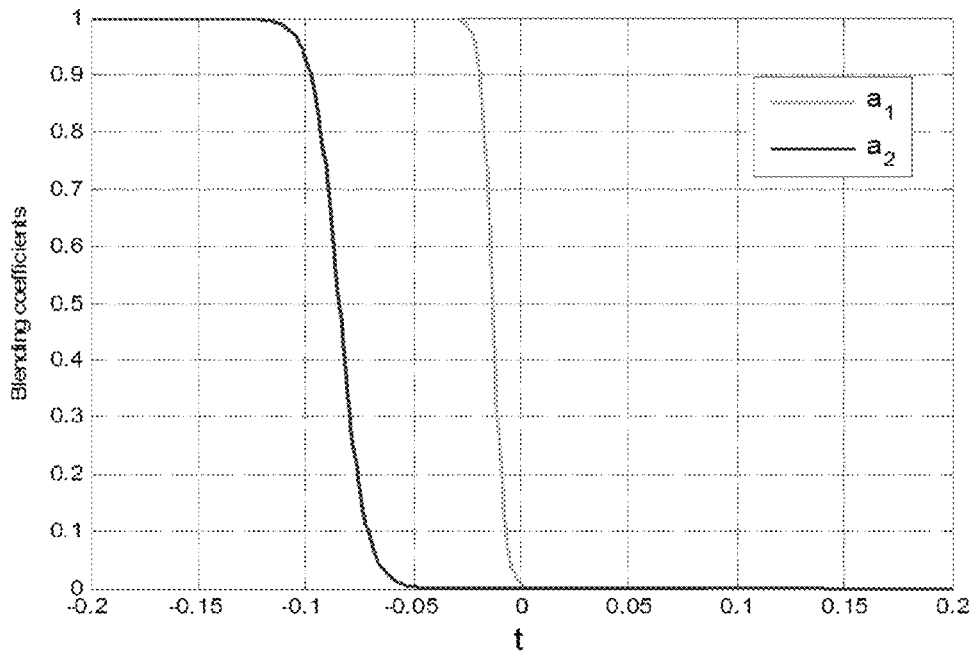
FIG. 2 is a graph depicting one or more aspects related to the present disclosure.

FIG. 2 is a graph depicting the above-described blending coefficients $a_1$ and $a_2$ as a function of the measure of fluid type t. As described above, the measure of fluid type t is based on the projection of the in-situ obtained spectral data onto the second eigenvector or principal component, which is determined based on the preexisting spectral data. Coefficients in the logistic function shown in Equation (30) may be optimized using a genetic algorithm, for example, such that the composition prediction may provide results across the possible range of fluids. As depicted in FIG. 2, when the measure of fluid type t is greater than about zero (0), the coefficients $a_1$ and $a_2$ have near-zero values, implying that B is close to $B_{oil}$. Similarly, B approximates $B_{gascond}$ when $a_1$ is close to 1, $a_2$ is close to 0, and the measure of fluid type t ranges between about −0.01 and about −0.03, and, B approximates $B_{gas}$ when $a_1$ is close to 1, $a_2$ is close to 1, and the measure of fluid type t is less than about −0.12.

Figure 3:
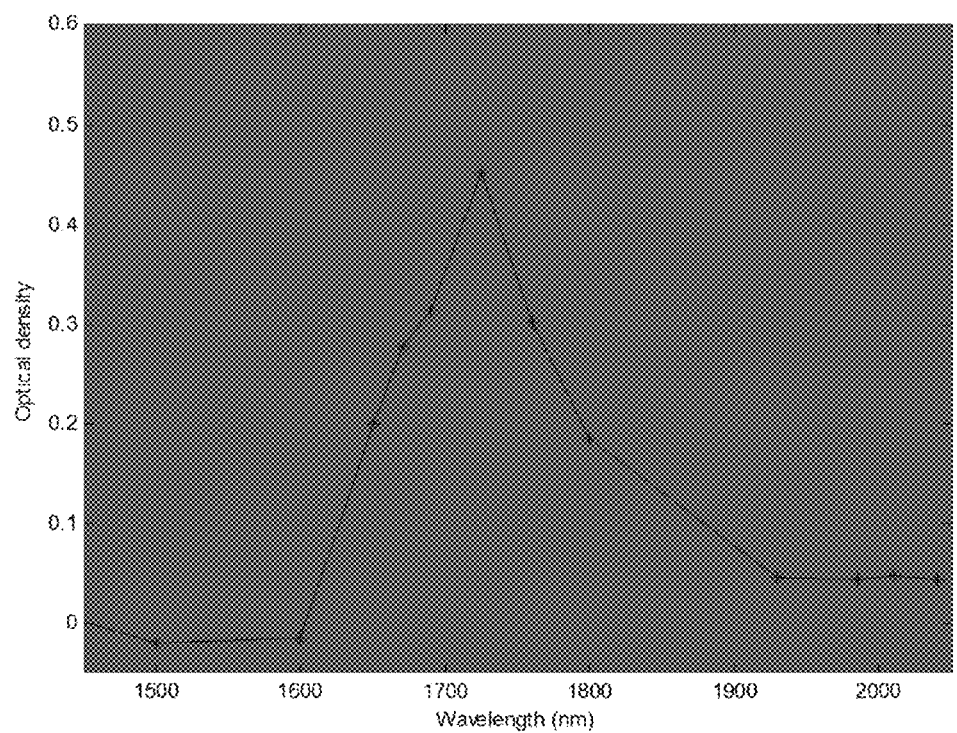
FIG. 3 is a graph depicting one or more aspects related to the present disclosure.
Figure 4:
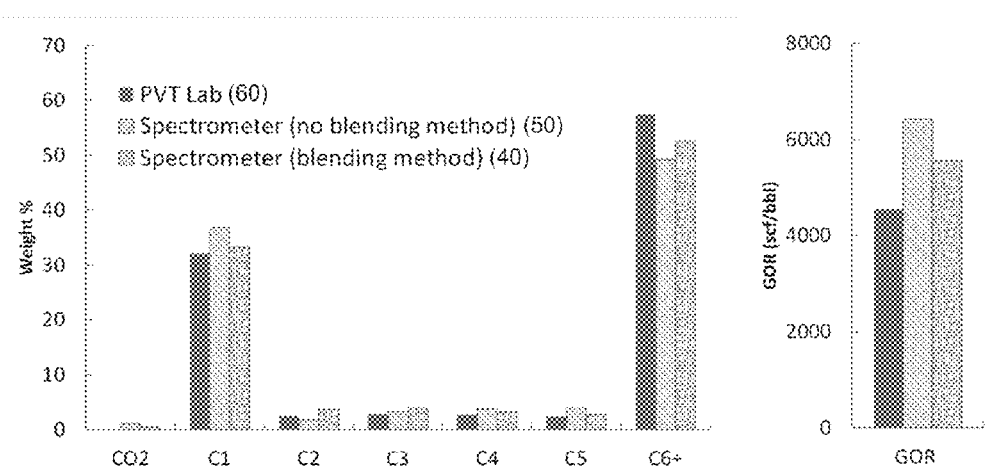
FIG. 4 is a chart depicting one or more aspects related to the present disclosure.

FIG. 3 is a graph depicting example optical spectrum of a downhole fluid measured with a downhole optical spectrometer during a sampling operation. Subsequent laboratory tests revealed the downhole fluid to be volatile oil. FIG. 4 is a chart depicting the estimated composition obtained utilizing the blending method (data 40) and the non-blending method (data 50) described above, in comparison with the laboratory results (data 60). The non-blending method utilized the mapping matrix of gas condensate for estimating composition, as the above-described fluid identification algorithm identified the sample fluid as gas condensate. For the blending method, blending coefficients were determined to be $a_1$=0.48 and $a_2$ approximately equal to 0, such that the blending was achieved with 48% of the mapping matrix for oil and 52% of the mapping matrix for gas condensate, as obtained for matrix blending utilizing Equation (29). As depicted in FIG. 4, the results obtained utilizing the above-described blending method more closely agree with the PVT laboratory results, relative to the results obtained utilizing the non-blending method, with respect to both composition components and GOR.

Note that the above analysis is presented in terms of DFA with respect to specific compositional components, namely: C1, C2, C3, C4, C5, C6+ and CO2. However, the above analysis and the rest of the present disclosure may also be applicable or readily adaptable to fluid analysis with respect to other compositional components, perhaps including C3-5, C6 and/or C7+, among others within the scope of the present disclosure.

After determining composition based on optical data as described above, various other parameters may be obtained based on the obtained composition. For example, the composition may be utilized to determine GOR of the formation fluid, such as via utilization of an artificial neural network (ANN), among other methods.

An ANN is a nonlinear statistical data modeling tool composed of a plurality of interconnected neuron-like processing units that relate input data to output data. An ANN can be trained to learn correlations or relationships between data to model complex global behavior among that data using neuron parameters (e.g., weighting values and bias values) and the connections between the neurons. An ANN has the ability to recognize patterns in data, adjust dynamically to changes, infer general rules from specific cases, and accept a large number of input variables. The example methods and apparatus described herein can be implemented using various ANN types, including a single-layer perceptron ANN and/or a multi-layer perceptron ANN. An ANN can be trained using training data in conjunction with a variety of training techniques. The ANN performance can be continuously improved by expanding the training data used to train the ANN and retraining the ANN on a periodic and/or aperiodic basis.

Figure 5:
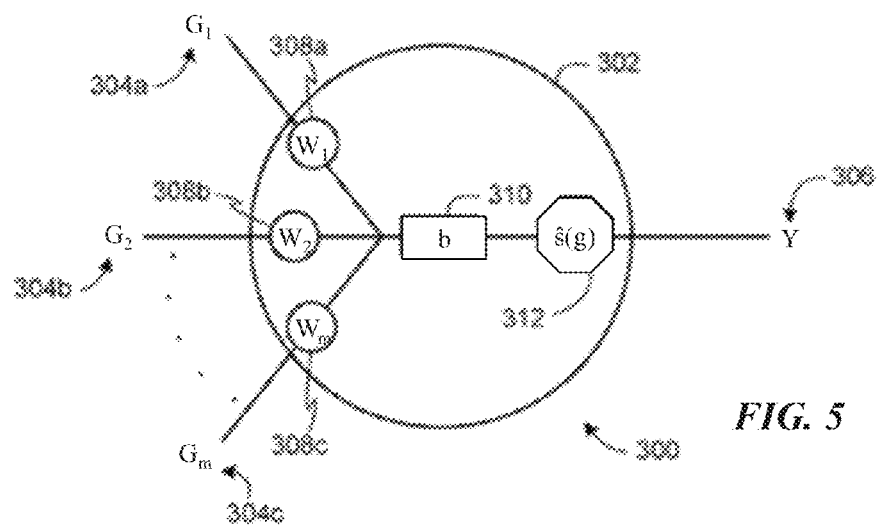
FIG. 5 is a schematic view of an artificial neural network (ANN) node according to one or more aspects of the present disclosure.

FIG. 5 depicts an example ANN node 300 having a neuron 302, a plurality of input interfaces 304a-c, and an output interface 306. One or more ANN nodes substantially similar or identical to the ANN node 300 can be used to implement the example methods and apparatus described herein. For example, the example methods and apparatus described herein can be implemented using an example ANN 400 of FIG. 6 having a plurality of nodes that may be substantially similar or identical to the example ANN node 300.

In the illustrated example of FIG. 5, each of the inputs $G_1$-$G_m$ 304a-c is provided with a respective one of a plurality of weighting values $W_1$-$W_m$ 308a-c, a bias value b 310, and an activation function ($\hat{s}(g)$) 312. The weighting values $W_1$-$W_m$ 308a-c are applied to the input values $G_1$-$G_m$ 304a-c to apply more or less weight to each of the input values $G_1$-$G_m$ 304a-c so that each value has a greater or a lesser effect on the output data (Y) at the output interface 306. The bias value b 310 is applied to the weighted sum of the input values $G_1$-$G_m$ 304a-c so that the input of the activation function 312 is biased. The activation function 312 may be chosen from various activation functions such as, for example, a sigmoid function.

To produce intended or optimum values at the output 306 for respective input values at the inputs $G_1$-$G_m$ 304a-c, the ANN node 300 is trained during a training phase to learn the values for the weighting values $W_1$-$W_m$ 308a-c and the bias value b 310. That is, during the training phase, the ANN node 300 determines the weighting values $W_1$-$W_m$ 308a-c and the bias value b 310 to quantify the correlations or relationships between input values at the inputs $G_1$-$G_m$ 304a-c and corresponding output values (Y) 306. In this manner, during a subsequent recognition (prediction) phase, the ANN node 300 can use the correlations or relationships indicated by the learned values for the weighting values $W_1$-$W_m$ 308a-c and the bias value b 310 to produce the intended output values based on provided input values.

Figure 6:
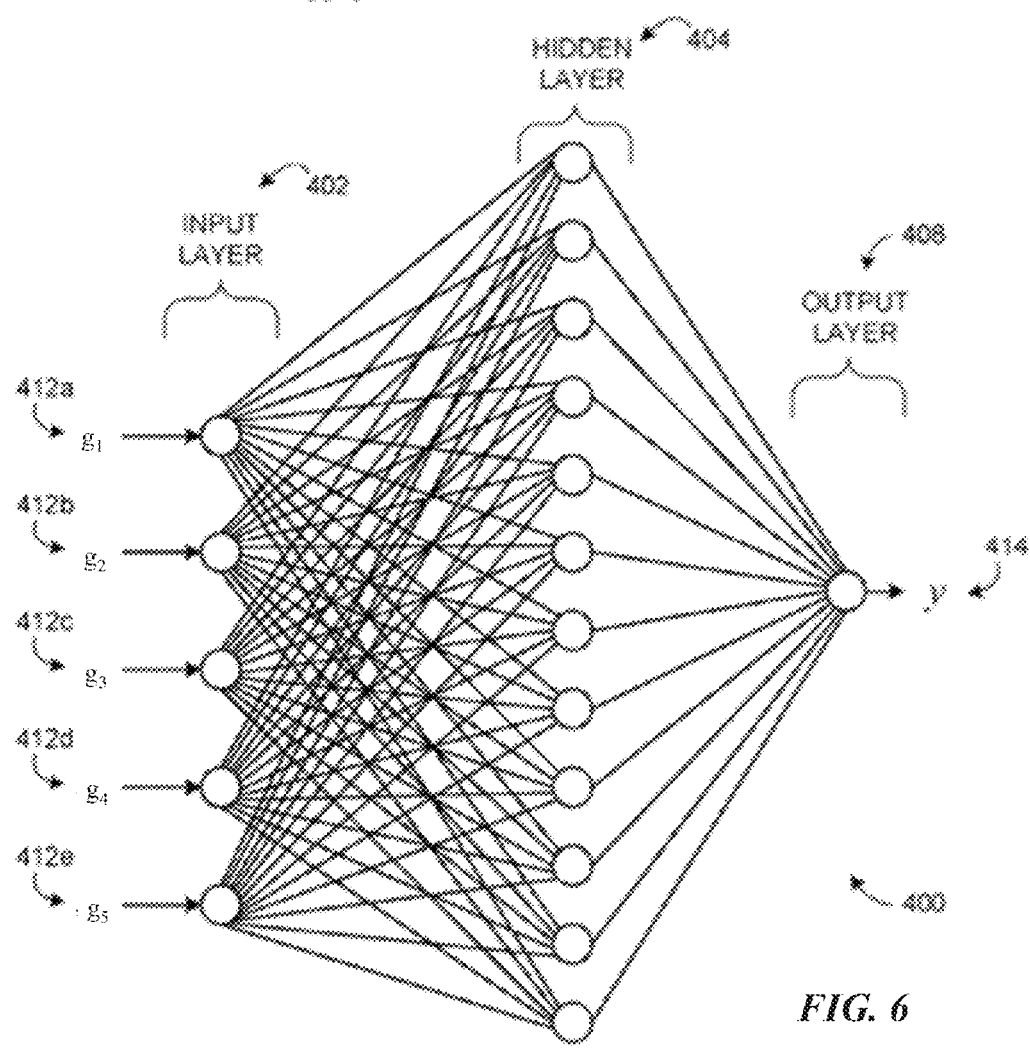
FIG. 6 is a schematic view of at least a portion of an ANN according to one or more aspects of the present disclosure.

The example ANN 400 of FIG. 6 is implemented using a feedforward multilayer perception (FF-MLP) ANN model. In the illustrated example, the example ANN 400 includes a plurality of layers, including an input layer 402, a hidden layer 404, and an output layer 408. Each of the layers 402, 404, and 408 is provided with one or more nodes, each of which includes inputs and outputs. Although not shown, the inputs are provided with weighting values and bias values similar to the weighting values $W_1$-$W_m$ 308a-c and the bias value b 310 of FIG. 5. The FF-MLP ANN 400 of FIG. 6 determines output values by progressively communicating or feeding values forward through the layers 402, 404, and 408. For example, each node of the input layer 402 may receive a respective one of a plurality of input values $g_1$-$g_5$ 412a-e and output a respective value to each of twelve (for example) nodes in the hidden layer 404. The nodes of the hidden layer 404 then generate respective output values based on the outputs from the input layer 402 and communicate their outputs to the node of the output layer 408. The output layer 408 node then generates an output value y 414 based on the outputs from the hidden layer 404. Although the illustrated example ANN 400 has one hidden layer and one output value, in other example implementations, an ANN may be implemented using more hidden layers and/or more output values.

In the illustrated example, the example ANN 400 is configured to estimate PVT properties of formation fluid samples. That is, the ANN 400 provides the estimated PVT property values at the output y 414. To generate estimated PVT property values, the input values $g_1$-$g_5$ 412a-e are component values that describe a multi-component composition of a formation fluid. For example, if the fluid composition of a multi-component fluid includes five components, each of the five components can be provided to a respective one of the inputs 412a-e of the example ANN 400, and the ANN 400 can output an estimated PVT value via the output layer 408. An example five-component formation fluid composition may include CO2, C1, C2, C3-C5, and C6+. However, other implementations may utilize other or additional components, such as in conjunction with the description above in which the compositional components include C1, C2, C3, C4, C5, C6+, and CO2. The concentration of each component can be determined as described above and then provided to the example ANN 400 to determine the output y 414.

To generate accurate output values at the output y 414, the example ANN 400 may be trained using training data including input values (e.g., component concentration values) and respective output values (e.g., PVT property values). During a training phase, the ANN 400 determines correlations or relationships between input values and output values by applying a first set of input values to the inputs $g_1$-$g_5$ 412a-e and adjusting the weighting values and bias values of each of the nodes of the layers 404 and 408 until the values at the output y 414 are substantially equal to true values (i.e., laboratory-measured values) corresponding to the first set of input values applied to the inputs $g_1$-$g_5$ 412a-e. In the illustrated example, the training input values and output values may be obtained from a training database of known data, derived using other methods. For example, a training database that may be used to train the example ANN 400 to determine estimated PVT property values may include laboratory-measured fluid composition and PVT data (e.g., input data and output data) of reservoir fluids from around the world. In addition, the database can also include laboratory-measured data from derivative fluids from intermediate steps of differential vaporization studies (for oils) and depletion studies (for gas condensates). In some example implementations, a training database can include data (e.g., input data and output data) corresponding to hundreds or thousands of discrete formation fluid samples.

In the illustrated example, the ANN 400 is implemented using an m-dimensional input vector (g) by an n-dimensional output vector (y) network in which m=5 (e.g., the mass fractions C1, C2, C3-C5, C6+, and CO2) and n=1 (e.g., the estimated GOR value). The relationship between the inputs $g_1$-$g_5$ 412a-e, the output y 414, the weighting values (e.g., the weighting values $W_1$-$W_m$ 308a-c of FIG. 5), and the bias values (e.g., the bias value b 310 of FIG. 5) of the ANN 400 is set forth in an ANN function of Equation (37) below.

$$y = s(W_L \cdot s\{W_{L-1} \cdot s[\ldots s(W_0 g + b_0)] + b_{L-1}\} + b_L) \tag{37}$$

In Equation (37), a layer quantity value (L) specifies the quantity of hidden layers in the ANN 400, a weight matrix ($W_L$) specifies a matrix of weighting values for a particular layer (L), and a bias vector ($b_L$) specifies a vector of biases for a particular layer (L).

In some example implementations, a single hidden layer with a sufficient number of nodes in the hidden layer is capable of approximating a continuous, differentiable function. Thus, if the layer quantity (L) is equal to one (i.e., L=1), the ANN function of Equation (37) can be expressed as shown in Equation (38) below.

$$y = s[W_1 \cdot s(W_0 g + b_0) + b_1] \tag{38}$$

In Equations (37) and (38) above, the activation function s(g) defines how the ANN 400 conditions input data to generate output data. The activation function (s(g)) can be defined as shown in Equations (39) and (40) below.

$$s(g) = \begin{bmatrix} \hat{s}(g_1) \\ \vdots \\ \hat{s}(g_m) \end{bmatrix} \tag{39}$$

where $$\hat{s}(g_i) = 1/[1 + \exp(-g_i)] \tag{40}$$

As shown in Equation (39), the activation function s(g) produces a vector of data generated using a logistic function or a sigmoid function $\hat{s}(g_i)$, which is defined in Equation (40) above. As shown in Equations (37)-(40), the ANN 400 generates output data at the output y 414 by performing two linear operations and two nonlinear operations.

To process input values within a particular range, the inputs to the ANN 400 (e.g., composition components if determining GOR) are normalized to a [0,1] range using Equation (41) set forth below.

$$\tilde{g}_i = (g_i - g_{i,min})/(g_{i,max} - g_{i,min}) \text{ where } i=1,m \tag{41}$$

In Equation (41), $g_{i,min}$ is the minimum value of the input $g_1$ in the training database, and $g_{i,max}$ is the maximum value of the input $g_1$ in the training database.

In some instances, the output values at the output y 414 are distributed over a wide numerical range. To normalize the output values, the ANN 400 can be configured to perform the logarithmic transformation function shown in Equation (42) below on the output values.

$$\tilde{y} = 0.8 \left\{ \frac{\ln(y) - \ln(y_{min})}{\ln(y_{max}) - \ln(y_{min})} \right\} + 0.1 \tag{42}$$

In a GOR example of Equation (42), $y_{min}$ is the minimum value of GOR in the training database, and $y_{max}$ is the maximum value of GOR in the training database. When using the ANN 400 to determine estimated GOR values, Equation (42) can be used to normalize GOR logarithms to a [0.1, 0.9] range to ensure that the output values at the output y 414 are within a [0, 1] range of the sigmoid function of Equation (40) above.

Using Equations (41) and (42) above, the ANN function of Equation (38) above can be expressed as shown in Equation (43) below.

$$\tilde{y} = s[W_1 \cdot s(W_0 \tilde{g} + b_0) + b_1] \tag{43}$$

In the illustrated, example, the ANN 400 is configured to determine an estimated GOR based on an output value ($\tilde{y}$) from Equation (43) based on Equation (44) below.

$$GOR = \exp\left\{ \frac{(\tilde{y} - 0.1)\{\ln(y_{max}) - \ln(y_{min})\}}{0.8} + \ln(y_{min}) \right\} \tag{44}$$

The ANN model 400 may be trained using a training database. During a training phase, the ANN 400 learns the underlying behavior of the training dataset stored in the training database. There are numerous algorithms available for training neural network models. The output values generated by the ANN 400 during the training phase are values for the elements of the weight matrices $W_L$ and vectors $b_L$. The ANN 400 may be trained using a portion of datapoints stored in the training database (e.g., a training set), and then validated using datapoints in a validation set that were not used for training. For example, 90% of the training datapoints of a database could be selected at random for training, and the remaining 10% could be used for validation of the ANN 400.

Another parameter that may be determined after determining composition based on optical data as described above is the formation volume factor (FVF). FVF is a volumetric ratio of crude oil at formation condition (i.e., live oil) $V_{LO}$ to its stock tank oil $V_{STO}$ at the surface. This live oil may represent the formation fluid in the formation or as it flows through the downhole tool while the downhole tool is disposed within the wellbore. The stock tank oil may represent the formation fluid at a surface condition of approximately 60° degrees F. and approximately 14.7 psia. The optical density of the stock tank oil at this standard condition may be expressed as set forth below in Equation (45).

$$OD_{STO} = \alpha_{STO} \cdot \rho_{STO} \cdot l = \alpha_{STO} \cdot (M_{STO}/V_{STO}) \cdot l \tag{45}$$

where $M_{STO}$ and $V_{STO}$ are respectively the mass and volume of the stock tank oil.

The optical density of the live oil at a particular temperature and pressure is defined as a linear combination of: (1) the optical spectra of its STO portion; and (2) the optical spectra of its gas components at the live oil condition. Optical spectra of the STO at the live oil condition is provided below in Equation (46).

$$OD_{STO}' = \alpha_{STO} \cdot \rho_{STO}' \cdot l = \alpha_{STO} \cdot (M_{STO}/V_{LO}) \cdot l \tag{46}$$

In Equation (46), $\rho_{STO}'$ represents the density of the stock tank oil at the formation (or flow line) temperature and pressure.

Optical spectra of the gas component of the live oil is provided as set forth below in Equation (47).

$$OD_{gas} = \Sigma_i \alpha_i \cdot (\mu_i \cdot \rho_i) \cdot l = \Sigma_i \alpha_i \cdot (\mu_i \cdot \rho_i / V_{LO}) \cdot l \tag{47}$$

In Equation (47), the index i represents each of the multiple components that make up the formation fluid (in vapor phase). As described above, these components may include C1, C2, C3, C4, C5, C6+, and CO2. In Equation (47), $\mu_i$ represents the vapor fraction of the component i.

The optical spectrum of the live oil is a linear combination of Equations (46) and (47), as set forth below in Equation (48).

$$OD_{LO} = (\alpha_{STO} \cdot M_{STO} + \Sigma_i \alpha_i \cdot \mu_i \cdot M_i) \cdot l / V_{LO} \tag{48}$$

In Equation (48), $\alpha_i$ is the absorption coefficient of component i (for i=C1, C2, C3, C4, C5, C6+, and CO2). Similarly, $M_i$ is the mass of component i, and $\mu_i$ is the vapor fraction of component i.

FVF is the volume ratio of live oil at formation condition to STO at standard (STO) condition. As noted above, live oil is the oil (with gas) that comes directly from the formation and flows through the downhole tool. Stock tank oil is the corresponding oil that remains after the sampled formation fluid is brought to the surface and the gas, liberated under surface conditions, is removed from the sample. From Equation (45), the STO volume is given as set forth below in Equation (49).

$$V_{STO} = \alpha_{STO} \cdot M_{STO} \cdot l / OD_{STO} \quad (49)$$

Likewise, Equation (48) can be rearranged to provide the live oil volume, as set forth below in Equation (50).

$$V_{LO} = (\alpha_{STO} \cdot M_{STO} + \Sigma_i \alpha_i \cdot \mu_i \cdot M_i) \cdot l / OD_{LO} \quad (50)$$

Dividing Equation (50) by Equation (49) then yields the estimated oil formation volume factor ($FVF_O$), as set forth below in Equation (51).

$$FVF_O = (OD_{STO}/OD_{LO})(1 + \Sigma_i \tilde{\alpha}_i \cdot \mu_i \cdot M_i / M_{STO}) \quad (51)$$

In Equation (51), $\tilde{\alpha}_i$ represents the absorption coefficient of the component i taken with respect to the absorption coefficient of the STO, as set forth below in Equation (52).

$$\tilde{\alpha}_i = \alpha_i / \alpha_{STO} \quad (52)$$

In addition, the mass of the stock tank oil ($M_{STO}$ of Equation (51)) may be defined in terms of the individual component masses $M_i$ and the respective vapor fractions $\mu_i$, as set forth below in Equation (53).

$$M_{STO} = \Sigma_k (1 - \mu_k) M_k \quad (53)$$

In Equation (53), k represents each of the components of the formation fluid (e.g., k=C1, C2, C3, C4, C5, C6+, and CO2). Combining Equations (51) and (53) results in Equation (54) set forth below.

$$FVF_O = (OD_{STO}/OD_{LO})(1 + \Sigma_i \tilde{\alpha}_i \cdot \mu_i \cdot \tilde{\rho}_i / (\Sigma_k (1 - \mu_k) \rho_k)) \quad (54)$$

The concentration $\tilde{\rho}_i$ in Equation (54) represents a relative concentration of each component taken with respect to the concentration of C6+. This relative concentration may be calculated by comparing the weight fraction w of each component with the weight fraction of C6+, as set forth below in Equation (55).

$$\tilde{\rho}_i = \rho_i / \rho_{C6+} = w_i / w_{C6+} \quad (55)$$

At this point, certain assumptions can be made regarding variables that determine FVF. For example, the vapor fractions $\mu_i$ of C1, C2, and CO2 at standard (STO) condition are equal to one, and the absorption coefficient $\alpha_i$ of CO2 in the wavelength range of 1600 nm to 1800 nm is approximately equal to zero, or is negligible in comparison to the absorption coefficients of the hydrocarbons. Applying these two assumptions to Equation (54) yields an expression for estimating FVF, as set forth below in Equation (56).

$$FVF_O = (OD_{STO}/OD_{LO}) \left[ 1 + \frac{\tilde{\alpha}_{C1}\tilde{\rho}_{C1} + \tilde{\alpha}_{C2}\tilde{\rho}_{C2} + \tilde{\alpha}_{C3}\mu_{C3}\tilde{\rho}_{C3} + \tilde{\alpha}_{C4}\mu_{C4}\tilde{\rho}_{C4} + \tilde{\alpha}_{C5}\mu_{C5}\tilde{\rho}_{C5} + \tilde{\alpha}_{C6+}\mu_{C6+}\tilde{\rho}_{C6+}}{(1-\mu_{C3})\tilde{\rho}_{C3} + (1-\mu_{C4})\tilde{\rho}_{C4} + (1-\mu_{C5})\tilde{\rho}_{C5} - \mu_{C6+} + 1} \right] \quad (56)$$

Another parameter that may be determined after determining composition based on optical data as described above is asphaltene content. For example, it is noted that the stock tank oil spectrum can be described as a linear combination of the asphaltene, resin, aromatic, and saturate spectra, as set forth below in Equation (57).

$$OD_{STO}(\lambda) = OD_{Asp}(\lambda) + OD_{Res}(\lambda) + OD_{Aro}(\lambda) + OD_{Sat}(\lambda) \quad (57)$$

$$= \alpha_{Asp}(\lambda) \cdot \rho_{Asp} \cdot l + \alpha_{Res}(\lambda) \cdot \rho_{Res} \cdot l + \alpha_{Aro}(\lambda) \cdot \rho_{Aro} \cdot l + \alpha_{Sat}(\lambda) \cdot \rho_{Sat} \cdot l$$

where components Asp, Res, Aro, and Sat correspond to asphaltenes, resins, aromatics, and saturates, respectively, and $\rho$ is the mass concentration of each component.

The absorption coefficients of aromatic and saturate components are generally negligible compared to those of asphaltene and resin components in much of the visible NIR wavelength range (e.g., 600-1600 nm). Consequently, the optical density of stock tank oil can be approximated as the sum of the optical densities of asphaltene and resin in this wavelength region, as set forth below in Equation (58).

$$OD_{STO}(\lambda) \approx OD_{Asp}(\lambda) + OD_{Res}(\lambda) = \alpha_{Asp}(\lambda) \cdot \rho_{Asp} \cdot l + \alpha_{Res}(\lambda) \cdot \rho_{Res} \cdot l \quad (58)$$

From Equation (58), the optical density of a stock tank oil can be written by using the absorption coefficients at a specified wavelength $\lambda$, the masses of asphaltene ($m_{Asp}$) and resin ($m_{Res}$) in the stock tank oil volume (V), and the optical path length (l), as set forth below in Equation (59).

$$OD_{STO}(\lambda) \approx \alpha_{Asp}(\lambda) \cdot (m_{Asp}/V) \cdot l + \alpha_{Res}(\lambda) \cdot (m_{Res}/V) \cdot l \quad (59)$$

where $\rho_i = m_i/V$.

Also, dividing both sides of Equation (59) with the density of the stock tank oil ($\rho_{STO}$) allows the equation to be rewritten as set forth below in Equation (60).

$$OD_{STO}(\lambda)/\rho_{STO} = \alpha_{Asp}(\lambda) \cdot (m_{Asp}/M_{STO}) \cdot l + \alpha_{Res}(\lambda) \cdot (m_{Res}/M_{STO}) \cdot l \quad (60)$$

where $\rho_{STO} = M_{STO}/V$.

Thus, the asphaltene content in mass fraction is related to the optical density of stock tank oil from Equation (60), as set forth below in Equation (61).

$$\frac{m_{Asp}}{M_{STO}} = \frac{1}{\alpha_{Asp}(\lambda) \cdot \rho_{STO} \cdot l} \cdot OD_{STO} - \frac{\alpha_{Res}(\lambda)}{\alpha_{Asp}(\lambda)} \cdot \frac{m_{Res}}{M_{STO}} = j \cdot OD_{STO} + k \quad (61)$$

where $$j = \frac{1}{\alpha_{Asp}(\lambda) \cdot \rho_{STO} \cdot l} \text{ and } k = -\frac{\alpha_{Res}(\lambda)}{\alpha_{Asp}(\lambda)} \cdot \frac{m_{Res}}{M_{STO}}$$

As may be seen from Equation (61), the coefficients j and k depend on $\alpha_i$, $\rho_{STO}$, and resin content ($m_{Res}/M_{STO}$), which are undetermined parameters. Also, in order to obtain optical density of a stock tank oil ($OD_{STO}$), live crude oil could be flashed at a standard, surface condition (e.g., 60 degrees F., 14.7 psia) to remove gaseous components and then allow the measurement of the optical density of the remaining liquid portion of the sample. In downhole environments, however, flashing a fluid sample while it is downhole to determine $OD_{STO}$ can be infeasible.

In such implementations, a relationship between asphaltene content and optical density of live crude oil can instead be derived using FVF, as described above, as set forth below in Equation (62).

$$\frac{m_{Asp}}{M_{STO}} = j \cdot OD_{STO}(\lambda) + k = j \cdot FVF_O \cdot OD_{LO}(\lambda) + k \quad (62)$$

The coefficients j and k can be determined to obtain asphaltene content from Equation (62). These coefficients can be calibrated and determined using a database containing optical spectra, formation volume factors, and asphaltene contents of crude oils. However, according to Equation (61), the coefficients j and k depend on the following parameters: stock tank oil density ($\rho_{STO}$); absorption coefficients of asphaltene ($\alpha_{Asp}$) and resin ($\alpha_{Res}$), since they are sample dependent; and the resin content ($m_{Res}/M_{STO}$). As such, the calibrated coefficients j and k have a range of variations associated with variation of these parameters in Equation (61).

Figure 7:
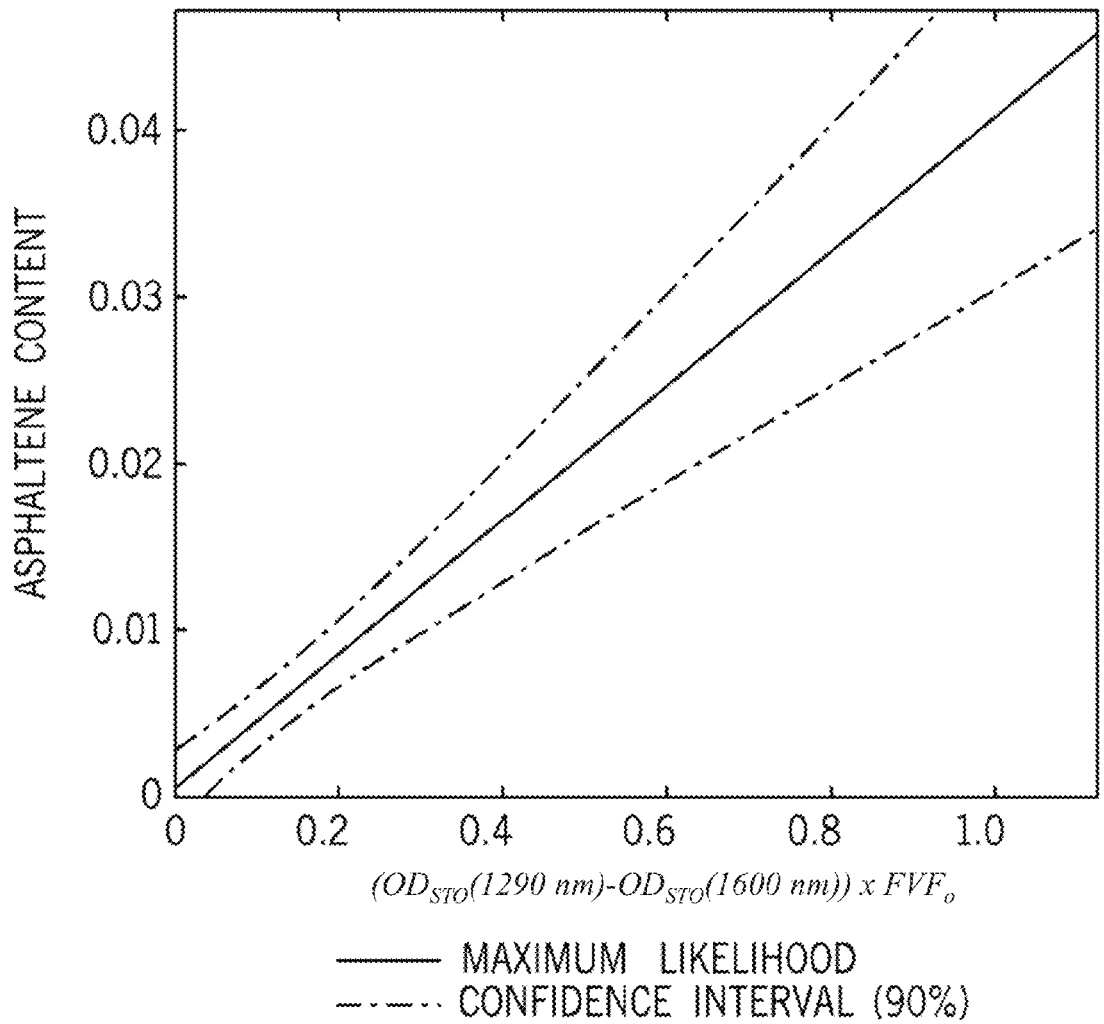
FIG. 7 is an example of a calibration curve of asphaltene content against optical density of stock tank oils according to one or more aspects of the present disclosure.

An example of a calibration curve of asphaltene content against optical density of stock tank oils estimated from optical densities of live crude oils and their formation volume factors in a database is depicted in FIG. 7. The database used for the calibration may include over one hundred crude oil spectra in a temperature range from about 75 degrees C. to about 175 degrees C., and in a pressure range from about 5,000 psi to about 20,000 psi. Other implementations, however, may rely on a different number of spectra across different temperature and/or pressure ranges.

In FIG. 7, the vertical axis indicates asphaltene content (expressed as a weight ratio) obtained from known techniques, such as in accordance with ASTM D2007-80 or ASTM D6560 standards promulgated by ASTM International, which are conventionally used in a Pressure-Volume-Temperature (PVT) laboratory. These standards may also be referred to as a modified IP 143 method. The horizontal axis is related to the estimated optical density of stock tank oils as described above. While some implementations may simply use the estimated optical density alone, in other implementations a difference between the optical densities of two channels may be used to avoid spectral offset due to light scattering by particles and refractive indices of samples. In the present example of FIG. 7, optical densities at 1290 nm and 1600 nm (i.e., $OD_{STO}(1290 \text{ nm})$ and $OD_{STO}(1600 \text{ nm})$) were used and scaled by the estimated formation volume factor for the calibration: ($OD_{STO}(1290 \text{ nm})$–$OD_{STO}(1600 \text{ nm})$)×$FVF_o$. The calibration curve can be obtained in other manners, such as by using a bootstrap resampling method or other resampling technique. The solid line in FIG. 7 indicates the maximum likelihood estimate, where j equals the slope of the solid line and k equals its y-intercept. The dashed lines indicate a 90% confidence interval associated with the range of variation of j and k, although other confidence levels could be used (e.g., a 95% confidence interval).

Figure 8:
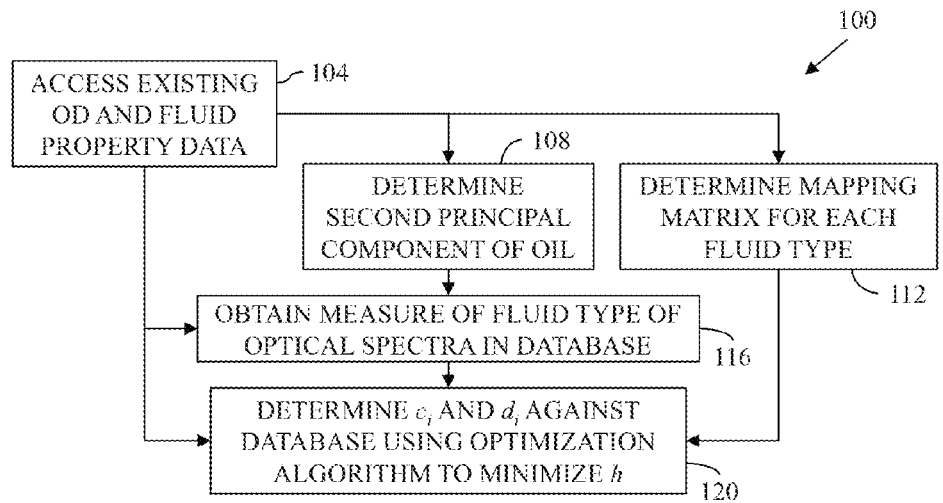
FIG. 8 is a flow-chart diagram of at least a portion of a method according to one or more aspects of the present disclosure.

FIG. 8 is a flow-chart diagram of a workflow and/or other type of method (100) according to one or more aspects described above. The method (100) utilizes the above-described aspects for build mapping matrices for each fluid type and perform calibration utilizing predetermined OD and other fluid property data, such as from a database, laboratory data, and/or other predetermined data. Thus, the method (100) includes accessing (104) such predetermined data to determine (108) the second principal component of oil, as described above. The existing data is also accessed (104) to determine (112) mapping matrices for the fluid types being analyzed, such as for oil, gas, and gas condensates, as described above. The database is also accessed (104) for utilizing with the determined (108) second principal component of oil to obtain (116) the measure t of each fluid type, as described above. The existing data is again accessed (104) for utilizing with the determined (112) mapping matrices and the obtained (116) measures for each fluid type to determine (120) the coefficients $c_i$ and $d_i$ using an optimization algorithm to minimize h, per Equations (30) and (30.1) described above.

Figure 9:
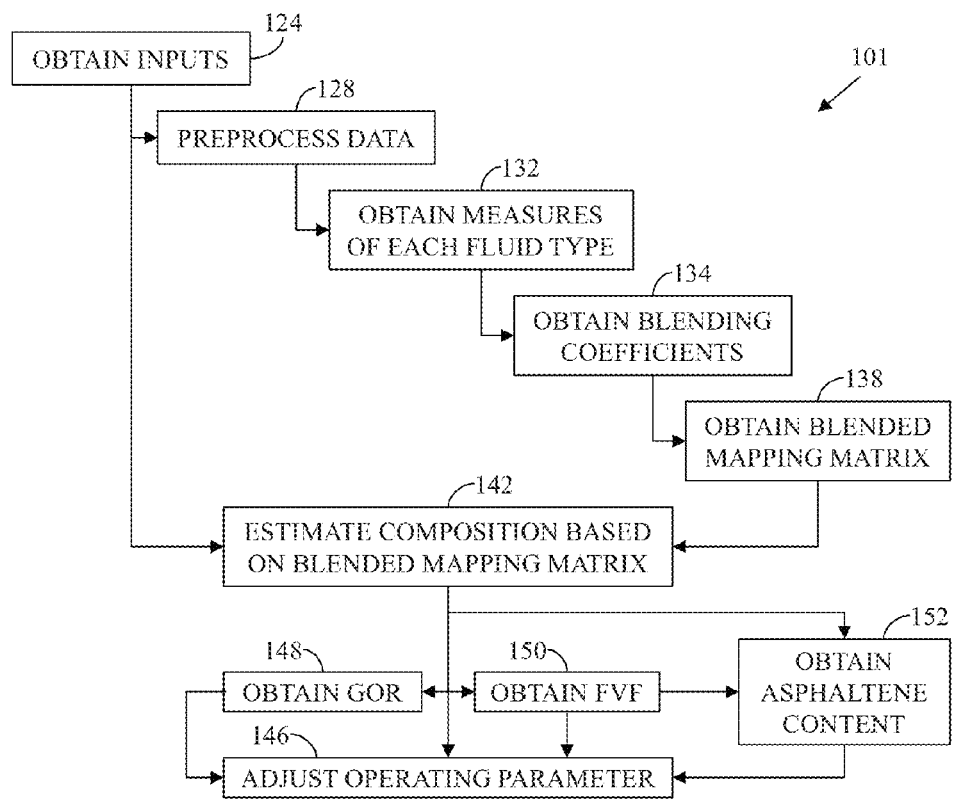
FIG. 9 is a flow-chart diagram of at least a portion of a method according to one or more aspects of the present disclosure.

FIG. 9 is a flow-chart diagram of a subsequent workflow and/or other type of method (101) according to one or more aspects described above. The method (101) utilizes the above-described aspects to predict the composition of sampled formation fluid, including aspects that may be explicitly described above but perhaps inherent or implicit in the following description.

The method (101) comprises obtaining (124) inputs, such as may comprise optical densities, perhaps converted to obtain the OD data corresponding to the appropriate number of channels (i.e., the number of channels of the downhole tool spectrometer). However, pressure, temperature, and/or other information may also be considered as inputs, among others.

Figure 10:
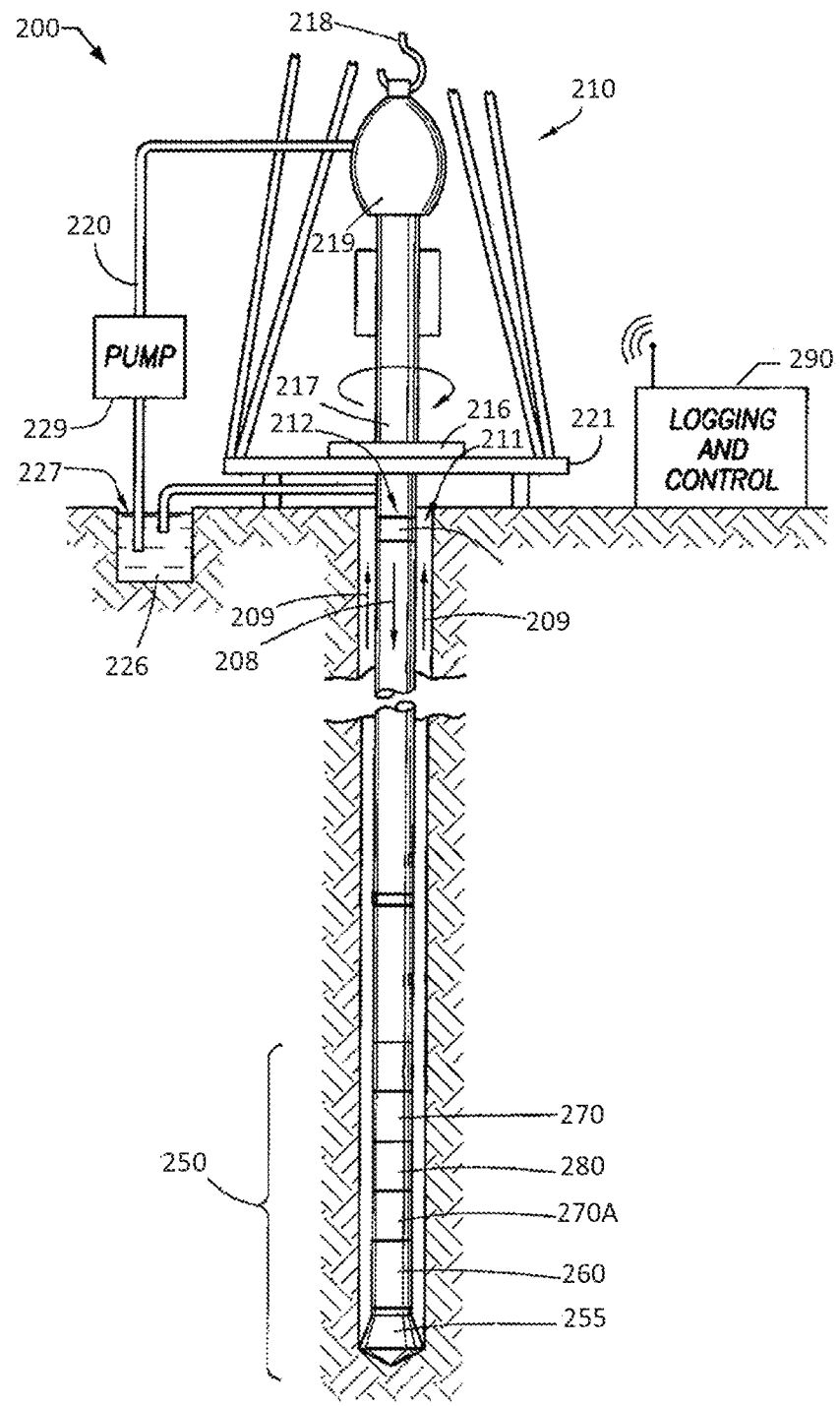
FIG. 10 is a schematic view of at least a portion of apparatus according to one or more aspects of the present disclosure.
Figure 11:
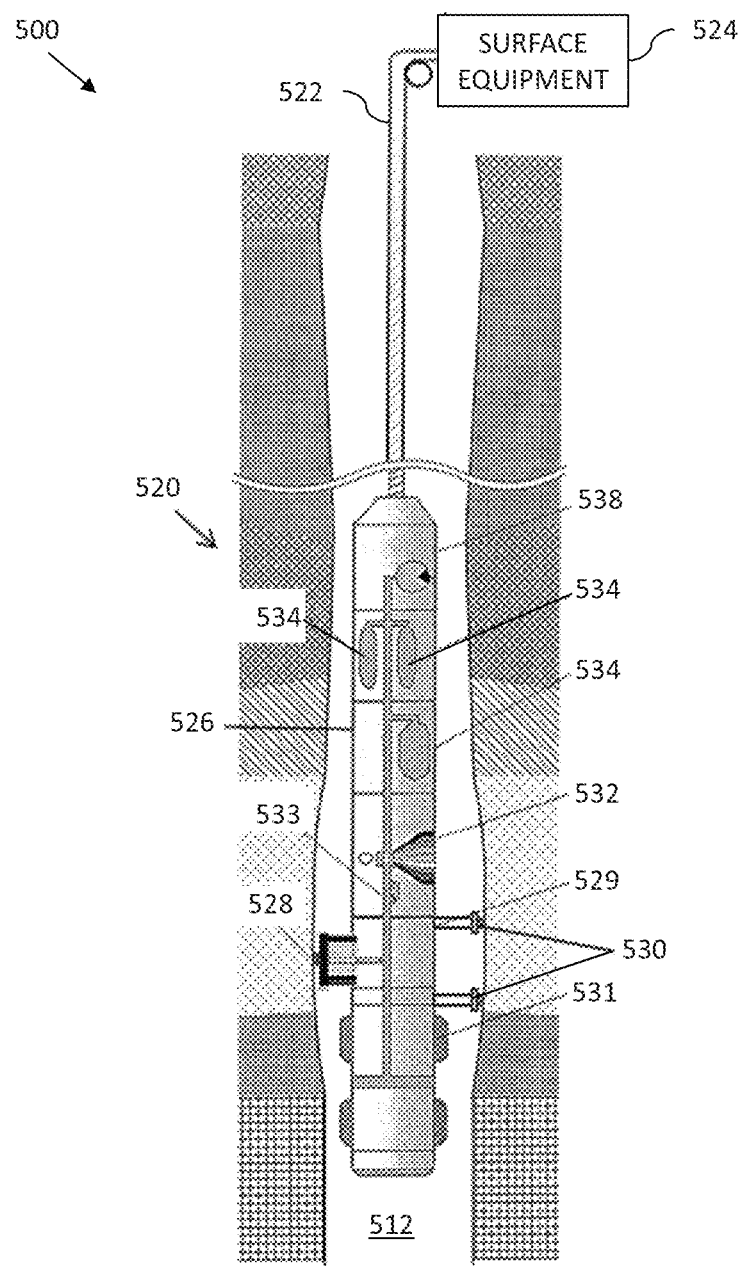
FIG. 11 is a schematic view of at least a portion of apparatus according to one or more aspects of the present disclosure.

The inputs may be obtained (124), at least in part, by operation of a downhole sampling tool conveyed along a borehole extending into a subterranean formation, wherein the downhole sampling tool may have one or more aspects in common with the apparatus 270/270A/280 shown in FIG. 10 and/or the apparatus 520 shown in FIG. 11, and may further be part of a BHA having one or more aspects in common with the BHA 250 shown in FIG. 10. The downhole sampling tool may be conveyed via wireline, one or more strings of tubulars (including drillstring and/or wired drill pipe), and/or other means. Once reaching the desired subterranean formation or station within the borehole, the downhole sampling tool obtains formation fluid from the formation.

The sampled formation fluid is then subjected to in-situ downhole analysis via a spectrometer of the downhole sampling tool, thereby obtaining spectral data representative of the sampled formation fluid. Such spectral data may form at least a portion of the inputs, such as may be obtained, at least in part, via a multi-channel optical sensor of the downhole formation fluid sampling apparatus, such as the optical detector 715 and/or a larger portion of the downhole fluid analyzer 700, each shown in FIG. 13 and described below. The sensor, detector, spectrometer, and/or analyzer utilized to obtain the spectral data may be or comprise a 20-channel spectrometer, although spectrometers utilizing more or less than 20 channels are also within the scope of the present disclosure. Obtaining the spectral data may also be performed while the downhole sampling apparatus pumps formation fluid from the formation downhole and through the flowline of the downhole sampling tool, or the spectral data may be obtained utilizing a static sample of formation fluid captured in a bypass line adjacent to the flowline and/or a chamber of the downhole formation fluid sampling apparatus.

The resulting optical spectra may be preprocessed (128). For example, the optical spectra may be de-watered. Water that may exist in the flowline can exhibit interference with hydrocarbon and CO2 peaks and therefore cause inaccuracy in the interpretation of the spectral data. The de-watering may be optional, however, and may be skipped if, for example, the presence of water is not observed. If the de-watering is performed, it may be performed utilizing various known and/or future-developed algorithm, process, and/or approach.

The preprocessing (128) may also comprise de-coloring, such as when the sampled formation fluid has color (e.g., when the sampled formation fluid comprises heavy oil(s)) that would otherwise cause inaccuracy in the interpretation of the spectral data. Preprocessing (128) the optical spectra may also or instead comprise de-scattering, such as when the sampled formation fluid comprises emulsions, bubbles, particles, precipitates, fines, and/or other contaminants that may otherwise cause inaccuracy in the interpretation of the spectral data. If the de-coloring and/or de-scattering are performed, they may be performed utilizing various known and/or future-developed algorithm, process, and/or approach.

The above-described measure t of each fluid type within the sample is then obtained (132). Such measures are then utilized to obtain (134) the blending coefficient corresponding to each fluid type. A blended mapping matrix is then obtained (138) utilizing the obtained (134) blending coefficients. The blended mapping matrix is then utilized to estimate (142) the composition of the sample.

The method (100) may also comprise adjusting (146) an operational parameter of the downhole sampling tool based on the estimated (142) composition. For example, such adjusting (146) may comprise initiating storage of a sample of the formation fluid flowing through the downhole formation fluid sampling apparatus based on the estimated (142) composition. Such adjusting (146) may also or instead comprise adjusting a rate of pumping of formation fluid into the downhole formation fluid sampling apparatus based on the estimated (142) composition.

The method (100) may also comprise obtaining (148) the GOR of the formation fluid based on the estimated (142) composition of the sample. For example, the process described above with respect to FIGS. 5 and 6 and Equations (37)-(44) may be utilized to obtain (148) the GOR based on the estimated (142) composition of the sample. In implementations of the method (100) that include obtaining (148) the GOR of the formation fluid and adjusting (146) an operational parameter of the downhole sampling tool, adjusting (146) the operational parameter of the downhole sampling tool may be based, at least in part, on the obtained (148) GOR.

The method (100) may also comprise obtaining (150) the FVF of the formation fluid based on the estimated (142) composition of the sample. For example, the process described above with respect to Equations (45)-(56) may be utilized to obtain (150) the FVF based on the estimated (142) composition of the sample. In implementations of the method (100) that include obtaining (150) the FVF of the formation fluid and adjusting (146) an operational parameter of the downhole sampling tool, adjusting (146) the operational parameter of the downhole sampling tool may be based, at least in part, on the obtained (150) FVF.

The method (100) may also comprise obtaining (152) the asphaltene content of the formation fluid based on the estimated (142) composition of the sample, and perhaps further based on the obtained (150) FVF. For example, the process described above with respect to Equations (57)-(62) may be utilized to obtain (152) the asphaltene content based on the estimated (142) composition of the sample and the obtained (150) FVF. In implementations of the method (100) that include obtaining (152) the asphaltene content of the formation fluid and adjusting (146) an operational parameter of the downhole sampling tool, adjusting (146) the operational parameter of the downhole sampling tool may be based, at least in part, on the obtained (152) asphaltene content.

FIG. 10 is a schematic view of an example wellsite system 200 in which one or more aspects of DFA disclosed herein may be employed. The wellsite 200 may be onshore or offshore. In the example system shown in FIG. 10, a borehole 211 is formed in subterranean formations by rotary drilling. However, other example systems within the scope of the present disclosure may also or instead utilize directional drilling.

As shown in FIG. 10, a drillstring 212 suspended within the borehole 211 comprises a bottom hole assembly 250 that includes a drill bit 255 at its lower end. The surface system includes a platform and derrick assembly 210 positioned over the borehole 211. The assembly 210 may comprise a rotary table 216, a kelly 217, a hook 218 and a rotary swivel 219. The drill string 212 may be suspended from a lifting gear (not shown) via the hook 218, with the lifting gear being coupled to a mast (not shown) rising above the surface. An example lifting gear includes a crown block whose axis is affixed to the top of the mast, a vertically traveling block to which the hook 218 is attached, and a cable passing through the crown block and the vertically traveling block. In such an example, one end of the cable is affixed to an anchor point, whereas the other end is affixed to a winch to raise and lower the hook 218 and the drillstring 212 coupled thereto. The drillstring 212 comprises one or more types of drill pipes threadedly attached one to another, perhaps including wired drilled pipe.

The drillstring 212 may be raised and lowered by turning the lifting gear with the winch, which may sometimes include temporarily unhooking the drillstring 212 from the lifting gear. In such scenarios, the drillstring 212 may be supported by blocking it with wedges in a conical recess of the rotary table 216, which is mounted on a platform 221 through which the drillstring 212 passes.

The drillstring 212 may be rotated by the rotary table 216, which engages the kelly 217 at the upper end of the drillstring 212. The drillstring 212 is suspended from the hook 218, attached to a traveling block (not shown), through the kelly 217 and the rotary swivel 219, which permits rotation of the drillstring 212 relative to the hook 218. Other example wellsite systems within the scope of the present disclosure may utilize a top drive system to suspend and rotate the drillstring 212.

The surface system may further include drilling fluid or mud 226 stored in a pit 227 formed at the wellsite. A pump 229 delivers the drilling fluid 226 to the interior of the drillstring 212 via a hose 220 coupled to a port in the swivel 219, causing the drilling fluid to flow downward through the drillstring 212 as indicated by the directional arrow 208. The drilling fluid exits the drillstring 212 via ports in the drill bit 255, and then circulates upward through the annulus region between the outside of the drillstring 212 and the wall of the borehole 211, as indicated by the directional arrows 209. In this manner, the drilling fluid 226 lubricates the drill bit 255 and carries formation cuttings up to the surface as it is returned to the pit 227 for recirculation.

A bottom hole assembly (BHA) 250 may comprise one or more specially-made drill collars near the drill bit 255. Each such drill collar may comprise one or more logging devices, thereby permitting downhole drilling conditions and/or various characteristic properties of the geological formation (e.g., such as layers of rock or other material) intersected by the borehole 211 to be measured as the borehole 211 is deepened. For example, the bottom hole assembly 250 may comprise a logging-while-drilling (LWD) module 270, a measurement-while-drilling (MWD) module 280, a rotary-steerable system and motor 260, and the drill bit 255. Of course, other BHA components, modules and/or tools are also within the scope of the present disclosure.

The LWD module 270 may be housed in a drill collar and may comprise one or more logging tools. It will also be understood that more than one LWD and/or MWD module can be employed, e.g., as represented at 270A. References herein to a module at the position of 270 may mean a module at the position of 270A as well. The LWD module 270 may comprise capabilities for measuring, processing and storing information, as well as for communicating with the surface equipment.

The MWD module 280 may also be housed in a drill collar and may comprise one or more devices for measuring characteristics of the drillstring 212 and/or drill bit 255. The MWD module 280 may further comprise an apparatus (not shown) for generating electrical power to be utilized by the downhole system. This may include a mud turbine generator powered by the flow of the drilling fluid 226, it being understood that other power and/or battery systems may also be employed. In the example shown in FIG. 10, the MWD module 280 comprises one or more of the following types of measuring devices: a weight-on-bit measuring device, a torque measuring device, a vibration measuring device, a shock measuring device, a stick slip measuring device, a direction measuring device, and an inclination measuring device, among others within the scope of the present disclosure. The wellsite system 200 also comprises a logging and control unit 290 communicably coupled in any appropriate manner to the LWD modules 270/270A and/or the MWD module 280.

The LWD modules 270/270A and/or the MWD module 280 comprise a downhole tool operable to obtain downhole a sample of fluid from the subterranean formation and perform DFA to estimate the composition of the obtained fluid sample. Such DFA is according to one or more aspects described elsewhere herein. The downhole fluid analyzer may then report the composition data to the logging and control unit 290.

FIG. 11 is a schematic view of another example operating environment of the present disclosure wherein a downhole tool 520 is suspended at the end of a wireline 522 at a wellsite having a borehole 512. The downhole tool 520 and wireline 522 are structured and arranged with respect to a service vehicle (not shown) at the wellsite. As with the system 200 shown in FIG. 10, the example system 500 of FIG. 11 may be utilized for downhole sampling and analysis of formation fluids. The system 500 includes the downhole tool 520, which may be used for testing earth formations and analyzing the composition of fluids from a formation, and also includes associated telemetry and control devices and electronics, and surface control and communication equipment 524. The downhole tool 520 is suspended in the borehole 512 from the lower end of the wireline 522, which may be a multi-conductor logging cable spooled on a winch (not shown). The wireline 522 is electrically coupled to the surface equipment 524.

The downhole tool 520 comprises an elongated body 526 encasing a variety of electronic components and modules, which are schematically represented in FIG. 11, for providing functionality to the downhole tool 520. A selectively extendible fluid admitting assembly 528 and one or more selectively extendible anchoring members 530 are respectively arranged on opposite sides of the elongated body 526. The fluid admitting assembly 528 is operable to selectively seal off or isolate selected portions of the borehole wall 512 such that pressure or fluid communication with the adjacent formation may be established. The fluid admitting assembly 528 may be or comprise a single probe module 529 and/or a packer module 531.

One or more fluid sampling and analysis modules 532 are provided in the tool body 526. Fluids obtained from the formation and/or borehole flow through a flowline 533, via the fluid analysis module or modules 532, and then may be discharged through a port of a pumpout module 538. In other embodiments, formation fluids in the flowline 533 may be directed to one or more fluid collecting chambers 534 for receiving and retaining the fluids obtained from the formation for transportation to the surface.

The fluid admitting assemblies, one or more fluid analysis modules, the flow path and the collecting chambers, and other operational elements of the downhole tool 520 may be controlled by one or more electrical control systems within the downhole tool 520 and/or the surface equipment 524. For example, such control system(s) may include processor capability for characterization of formation fluids in the downhole tool 520 according to one or more aspects of the present disclosure. Methods within the scope of the present disclosure may be embodied in one or more computer programs that run in a processor located, for example, in the downhole tool 520 and/or the surface equipment 524. Such programs may utilize data received from, for example, the fluid sampling and analysis module 532, via the wireline cable 522, and to transmit control signals to operative elements of the downhole tool 520. The programs may be stored on a suitable computer usable storage medium associated with the one or more processors of the downhole tool 520 and/or surface equipment 524, or may be stored on an external computer usable storage medium that is electronically coupled to such processor(s). The storage medium may be any one or more of known or future-developed storage media, such as a magnetic disk, an optically readable disk, flash memory or a readable device of any other kind, including a remote storage device coupled over a switched telecommunication link, among others.

FIGS. 10 and 11 illustrate mere examples of environments in which one or more aspects of the present disclosure may be implemented. For example, in addition to the drillstring environment of FIG. 10 and the wireline environment of FIG. 11, one or more aspects of the present disclosure may be applicable or readily adaptable for implementation in other environments utilizing other means of conveyance within the wellbore, including coiled tubing, TLC, slickline, and others.

Figure 12:
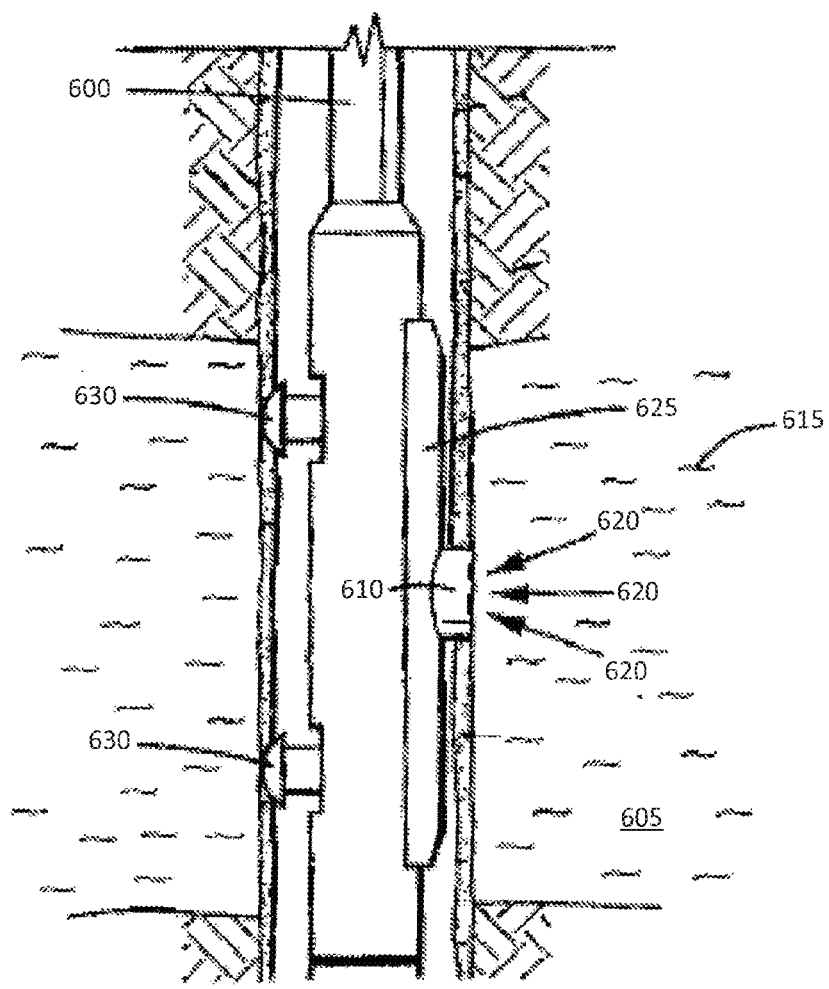
FIG. 12 is a schematic view of at least a portion of apparatus according to one or more aspects of the present disclosure.

An example downhole tool or module 600 that may be utilized in the example systems 200 and 500 of FIGS. 10 and 11, respectively, such as to obtain a sample of fluid from a subterranean formation 505 and perform DFA to estimate the composition of the obtained fluid sample, is schematically shown in FIG. 12. The tool 600 is provided with a probe 610 for establishing fluid communication with the formation 605 and drawing formation fluid 615 into the tool, as indicated by arrows 620. The probe 610 may be positioned in a stabilizer blade 625 of the tool 600 and extended therefrom to engage the borehole wall. The stabilizer blade 625 may be or comprise one or more blades that are in contact with the borehole wall. The tool 600 may comprise backup pistons 630 operable to press the tool 600 and, thus, the probe 610 into contact with the borehole wall. Fluid drawn into the tool 600 via the probe 610 may be measured to determine, for example, pretest and/or pressure parameters. Additionally, the tool 600 may be provided with chambers and/or other devices for collecting fluid samples for retrieval at the surface.

Figure 13:
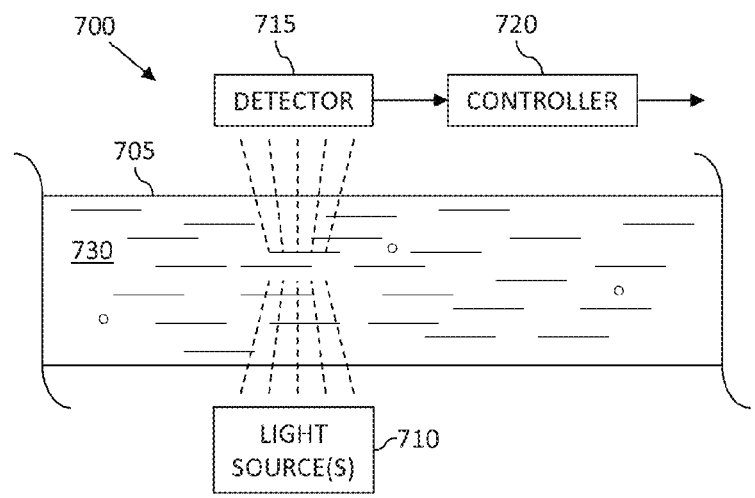
FIG. 13 is a schematic view of at least a portion of apparatus according to one or more aspects of the present disclosure.

An example downhole fluid analyzer 700 that may be used to implement DFA in the example downhole tool 600 shown in FIG. 12 is schematically shown in FIG. 13. The downhole fluid analyzer 700 may be part of or otherwise work in conjunction with a downhole tool operable to obtain a sample of fluid 730 from the formation, such as the downhole tools/modules shown in FIGS. 10-12. For example, a flowline 705 of the downhole tool may extend past an optical spectrometer having one or more light sources 710 and a detector 715. The detector 715 senses light that has transmitted through the formation fluid 730 in the flowline 705, resulting in optical spectra that may be utilized according to one or more aspects of the present disclosure. For example, a controller 720 associated with the downhole fluid analyzer 700 and/or the downhole tool may utilize measured optical spectra to estimate the composition of the formation fluid 730 in the flowline according to one or more aspects of DFA introduced herein. The resulting information may then be reported via any form of telemetry to surface equipment, such as the logging and control unit 290 shown in FIG. 10 or the surface equipment 524 shown in FIG. 11. Moreover, the downhole fluid analyzer 700 may perform the bulk of its processing downhole and report just a relatively small amount of measurement data up to the surface. Thus, the downhole fluid analyzer 700 may provide high-speed (e.g., real time) DFA measurements using a relatively low bandwidth telemetry communication link. As such, the telemetry communication link may be implemented by most types of communication links, unlike conventional DFA techniques that utilize high-speed communication links to transmit high-bandwidth signals to the surface.

Figure 14:
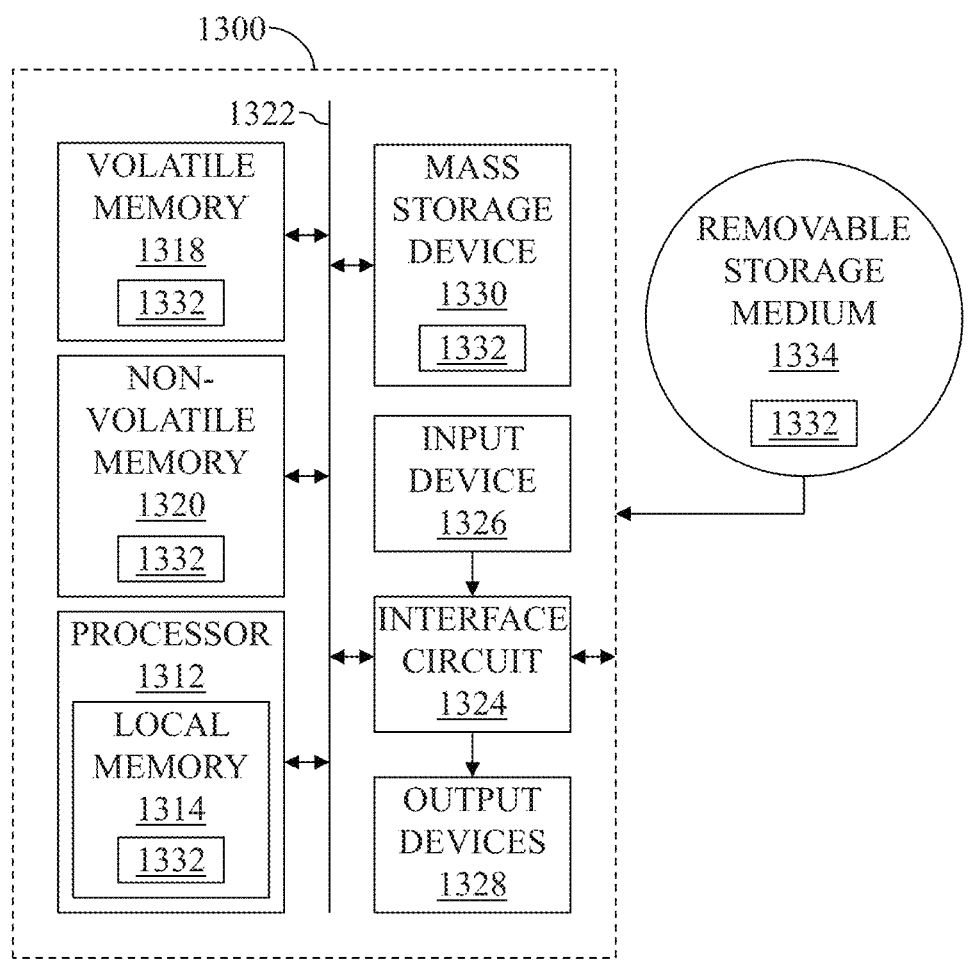
FIG. 14 is a schematic view of at least a portion of apparatus according to one or more aspects of the present disclosure.

FIG. 14 is a schematic view of at least a portion of apparatus according to one or more aspects of the present disclosure. The apparatus is or comprises a processing system 1300 that may execute example machine-readable instructions to implement at least a portion of one or more of the methods and/or processes described herein, and/or to implement a portion of one or more of the example downhole tools described herein. The processing system 1300 may be or comprise, for example, one or more processors, controllers, special-purpose computing devices, servers, personal computers, personal digital assistant ("PDA") devices, smartphones, internet appliances, and/or other types of computing devices. Moreover, while it is possible that the entirety of the processing system 1300 shown in FIG. 14 is implemented within downhole apparatus, such as the LWD module 270/270A and/or MWD module 280 shown in FIG. 10, the fluid sampling and analysis module 532 shown in FIG. 11, the controller 720 shown in FIG. 13, other components shown in one or more of FIGS. 10-13, and/or other downhole apparatus, it is also contemplated that one or more components or functions of the processing system 1300 may be implemented in wellsite surface equipment, perhaps including the logging and control unit 290 shown in FIG. 10, the surface equipment 524 shown in FIG. 11, and/or other surface equipment.

The processing system 1300 may comprise a processor 1312 such as, for example, a general-purpose programmable processor. The processor 1312 may comprise a local memory 1314, and may execute coded instructions 1332 present in the local memory 1314 and/or another memory device. The processor 1312 may execute, among other things, machine-readable instructions or programs to implement the methods and/or processes described herein. The programs stored in the local memory 1314 may include program instructions or computer program code that, when executed by an associated processor, enable surface equipment and/or downhole controller and/or control system to perform tasks as described herein. The processor 1312 may be, comprise, or be implemented by one or a plurality of processors of various types suitable to the local application environment, and may include one or more of general-purpose computers, special-purpose computers, microprocessors, digital signal processors ("DSPs"), field-programmable gate arrays ("FPGAs"), application-specific integrated circuits ("ASICs"), and processors based on a multi-core processor architecture, as non-limiting examples. Of course, other processors from other families are also appropriate.

The processor 1312 may be in communication with a main memory, such as may include a volatile memory 1318 and a non-volatile memory 1320, perhaps via a bus 1322 and/or other communication means. The volatile memory 1318 may be, comprise, or be implemented by random access memory (RAM), static random access memory (SRAM), synchronous dynamic random access memory (SDRAM), dynamic random access memory (DRAM), RAMBUS dynamic random access memory (RDRAM) and/or other types of random access memory devices. The non-volatile memory 1320 may be, comprise, or be implemented by read-only memory, flash memory and/or other types of memory devices. One or more memory controllers (not shown) may control access to the volatile memory 1318 and/or the non-volatile memory 1320.

The processing system 1300 may also comprise an interface circuit 1324. The interface circuit 1324 may be, comprise, or be implemented by various types of standard interfaces, such as an Ethernet interface, a universal serial bus (USB), a third generation input/output (3GIO) interface, a wireless interface, and/or a cellular interface, among others. The interface circuit 1324 may also comprise a graphics driver card. The interface circuit 1324 may also comprise a communication device such as a modem or network interface card to facilitate exchange of data with external computing devices via a network (e.g., Ethernet connection, digital subscriber line ("DSL"), telephone line, coaxial cable, cellular telephone system, satellite, etc.).

One or more input devices 1326 may be connected to the interface circuit 1324. The input device(s) 1326 may permit a user to enter data and commands into the processor 1312. The input device(s) 1326 may be, comprise, or be implemented by, for example, a keyboard, a mouse, a touchscreen, a track-pad, a trackball, an isopoint, and/or a voice recognition system, among others.

One or more output devices 1328 may also be connected to the interface circuit 1324. The output devices 1328 may be, comprise, or be implemented by, for example, display devices (e.g., a liquid crystal display or cathode ray tube display (CRT), among others), printers, and/or speakers, among others.

The processing system 1300 may also comprise one or more mass storage devices 1330 for storing machine-readable instructions and data. Examples of such mass storage devices 1330 include floppy disk drives, hard drive disks, compact disk (CD) drives, and digital versatile disk (DVD) drives, among others. The coded instructions 1332 may be stored in the mass storage device 1330, the volatile memory 1318, the non-volatile memory 1320, the local memory 1314, and/or on a removable storage medium 1334, such as a CD or DVD. Thus, the modules and/or other components of the processing system 1300 may be implemented in accordance with hardware (embodied in one or more chips including an integrated circuit such as an application specific integrated circuit), or may be implemented as software or firmware for execution by a processor. In particular, in the case of firmware or software, the embodiment can be provided as a computer program product including a computer readable medium or storage structure embodying computer program code (i.e., software or firmware) thereon for execution by the processor.

In view of the entirety of the present disclosure, including the figures and the claims below, a person having ordinary skill in the art will readily appreciate that the present disclosure introduces a method comprising: obtaining in-situ optical spectral data associated with a formation fluid flowing through a downhole formation fluid sampling apparatus; estimating, based on the obtained optical spectra data, a plurality of measures each relating the formation fluid to a corresponding one of a plurality of different fluid types; determining, based on the plurality of measures, a plurality of blending coefficients each corresponding to a different one of the plurality of different fluid types; obtaining a blended mapping matrix utilizing the plurality of blending coefficients and a plurality of predetermined mapping matrices each corresponding to a different one of the plurality of different fluid types; and predicting a parameter of the formation fluid flowing through the downhole formation fluid sampling apparatus based on a projection of the obtained spectral data onto the blended mapping matrix.

The method may further comprise obtaining, based on the obtained optical spectra data, the plurality of predetermined mapping matrices.

The predicted parameter may be a fluid property parameter.

The spectral data associated with the formation fluid flowing through the downhole formation fluid sampling apparatus may be obtained at least in part via a multi-channel optical sensor of the downhole formation fluid sampling apparatus, wherein the multi-channel optical sensor of the downhole formation fluid sampling apparatus may comprise at least one spectrometer.

Each of the plurality of predetermined mapping matrices may represent a linear relationship between preexisting spectral data and relative concentrations of predetermined compositional components of a plurality of known compositions. In such implementations, the plurality of different fluid types may comprise oil, gas, and gas condensate. The plurality of predetermined mapping matrices may comprise: a first fluid type mapping matrix corresponding to compositions having a predominant fluid type of oil; a second fluid type mapping matrix corresponding to compositions having a predominant fluid type of gas; and a third fluid type mapping matrix corresponding to compositions having a predominant fluid type of gas condensate.

Estimating the plurality of measures of each of the plurality of fluid types may comprise projecting the obtained spectra data onto a plurality of loading vectors of each fluid type. The method may further comprise obtaining the plurality of loading vectors utilizing principal component analysis (PCA) of the preexisting spectral data associated with a known fluid type.

Determining the plurality of blending coefficients may be further based on a predetermined logistic function having logistic function coefficients determined utilizing preexisting spectral data.

The predicted parameter of the formation fluid flowing through the downhole formation fluid sampling apparatus may be fluid composition.

The method may further comprise conveying the downhole formation fluid sampling apparatus within a wellbore extending into the formation, wherein the conveying may be via at least one of wireline and a string of tubulars.

The method may further comprise adjusting an operating parameter of the downhole formation fluid sampling apparatus based on the predicted parameter. Adjusting an operating parameter of the downhole formation fluid sampling apparatus based on the predicted parameter may comprise at least one of: initiating storage of a sample of the formation fluid flowing through the downhole formation fluid sampling apparatus based on the predicted parameter; and adjusting a rate of pumping of formation fluid into the downhole formation fluid sampling apparatus based on the predicted parameter.

The present disclosure also introduces an apparatus comprising: a downhole tool operable within a wellbore extending from a wellsite surface into a subterranean formation; and surface equipment disposed at the wellsite surface and in communication with the downhole tool, wherein the downhole tool and the surface equipment are collectively operable to: obtain in-situ optical spectral data associated with a formation fluid flowing through the downhole tool; estimate, based on the obtained optical spectra data, a plurality of measures each relating the formation fluid to a corresponding one of a plurality of different fluid types; determine, based on the plurality of measures, a plurality of blending coefficients each corresponding to a different one of the plurality of different fluid types; obtain a blended mapping matrix utilizing the plurality of blending coefficients and a plurality of predetermined mapping matrices each corresponding to a different one of the plurality of different fluid types; and predict a parameter of the formation fluid flowing through the downhole tool based on a projection of the obtained spectral data onto the blended mapping matrix.

The predicted parameter may be a fluid property parameter. The spectral data associated with the formation fluid flowing through the downhole tool may be obtained at least in part via a multi-channel optical sensor of the downhole tool, wherein the multi-channel optical sensor of the downhole tool may comprise at least one spectrometer.

The predicted parameter of the formation fluid flowing through the downhole tool may be fluid composition.

The downhole tool and the surface equipment may be further collectively operable to adjust an operating parameter of the downhole tool based on the predicted parameter. Adjusting an operating parameter of the downhole tool based on the predicted parameter may comprise at least one of: initiating storage of a sample of the formation fluid flowing through the downhole tool based on the predicted parameter; and adjusting a rate of pumping of formation fluid into the downhole tool based on the predicted parameter.

The foregoing outlines features of several embodiments so that a person having ordinary skill in the art may better understand the aspects of the present disclosure. A person having ordinary skill in the art should appreciate that they may readily use the present disclosure as a basis for designing or modifying other processes and structures for carrying out the same functions and/or achieving the same benefits of the embodiments introduced herein. A person having ordinary skill in the art should also realize that such equivalent constructions do not depart from the spirit and scope of the present disclosure, and that they may make various changes, substitutions and alterations herein without departing from the spirit and scope of the present disclosure.

The Abstract at the end of this disclosure is provided to comply with 37 C.F.R. §1.72(b) to permit the reader to quickly ascertain the nature of the technical disclosure. It is submitted with the understanding that it will not be used to interpret or limit the scope or meaning of the claims.

What is claimed is:

1. A method, comprising:
   obtaining in-situ optical spectral data associated with a formation fluid flowing through a downhole formation fluid sampling apparatus;
   estimating, based on the obtained optical spectra data, a plurality of measures each relating the formation fluid to a corresponding one of a plurality of different fluid types;
   determining, based on the plurality of measures, a plurality of blending coefficients each corresponding to a different one of the plurality of different fluid types;
   obtaining a blended mapping matrix utilizing the plurality of blending coefficients and a plurality of predetermined mapping matrices each corresponding to a different one of the plurality of different fluid types; and
   predicting a parameter of the formation fluid flowing through the downhole formation fluid sampling apparatus based on a projection of the obtained spectral data onto the blended mapping matrix.

2. The method of claim 1 further comprising obtaining, based on the obtained optical spectra data, the plurality of predetermined mapping matrices.

3. The method of claim 1 wherein the predicted parameter is a fluid property parameter.

4. The method of claim 1 wherein the spectral data associated with the formation fluid flowing through the downhole formation fluid sampling apparatus is obtained at least in part via a multi-channel optical sensor of the downhole formation fluid sampling apparatus, wherein the multi-channel optical sensor of the downhole formation fluid sampling apparatus comprises at least one spectrometer.

5. The method of claim 1 wherein each of the plurality of predetermined mapping matrices represents a linear relationship between preexisting spectral data and relative concentrations of predetermined compositional components of a plurality of known compositions.

6. The method of claim 5 wherein the plurality of different fluid types comprises oil, gas, and gas condensate.

7. The method of claim 6 wherein the plurality of predetermined mapping matrices comprises:
   a first fluid type mapping matrix corresponding to compositions having a predominant fluid type of oil;
   a second fluid type mapping matrix corresponding to compositions having a predominant fluid type of gas; and
   a third fluid type mapping matrix corresponding to compositions having a predominant fluid type of gas condensate.

8. The method of claim 1 wherein estimating the plurality of measures of each of the plurality of fluid types comprises projecting the obtained spectra data onto a plurality of loading vectors of each fluid type.

9. The method of claim 8 further comprising obtaining the plurality of loading vectors utilizing principal component analysis (PCA) of the preexisting spectral data associated with a known fluid type.

10. The method of claim 1 wherein determining the plurality of blending coefficients is further based on a predetermined logistic function having logistic function coefficients determined utilizing preexisting spectral data.

11. The method of claim 1 wherein the predicted parameter of the formation fluid flowing through the downhole formation fluid sampling apparatus is fluid composition.

12. The method of claim 1 further comprising conveying the downhole formation fluid sampling apparatus within a wellbore extending into the formation, wherein the conveying is via at least one of wireline and a string of tubulars.

13. The method of claim 1 further comprising adjusting an operating parameter of the downhole formation fluid sampling apparatus based on the predicted parameter.

14. The method of claim 13 wherein adjusting an operating parameter of the downhole formation fluid sampling apparatus based on the predicted parameter comprises at least one of:
   initiating storage of a sample of the formation fluid flowing through the downhole formation fluid sampling apparatus based on the predicted parameter; and
   adjusting a rate of pumping of formation fluid into the downhole formation fluid sampling apparatus based on the predicted parameter.

15. An apparatus, comprising:
   a downhole tool operable within a wellbore extending from a wellsite surface into a subterranean formation; and
   surface equipment disposed at the wellsite surface and in communication with the downhole tool, wherein the downhole tool and the surface equipment are collectively operable to:
      obtain in-situ optical spectral data associated with a formation fluid flowing through the downhole tool;
      estimate, based on the obtained optical spectra data, a plurality of measures each relating the formation fluid to a corresponding one of a plurality of different fluid types;
      determine, based on the plurality of measures, a plurality of blending coefficients each corresponding to a different one of the plurality of different fluid types;
      obtain a blended mapping matrix utilizing the plurality of blending coefficients and a plurality of predetermined mapping matrices each corresponding to a different one of the plurality of different fluid types; and
      predict a parameter of the formation fluid flowing through the downhole tool based on a projection of the obtained spectral data onto the blended mapping matrix.

16. The apparatus of claim 15 wherein the predicted parameter is a fluid property parameter.

17. The apparatus of claim 15 wherein the spectral data associated with the formation fluid flowing through the downhole tool is obtained at least in part via a multi-channel optical sensor of the downhole tool, wherein the multi-channel optical sensor of the downhole tool comprises at least one spectrometer.

18. The apparatus of claim 15 wherein the predicted parameter of the formation fluid flowing through the downhole tool is fluid composition.

19. The apparatus of claim 15 wherein the downhole tool and the surface equipment are further collectively operable to adjust an operating parameter of the downhole tool based on the predicted parameter.

20. The apparatus of claim 19 wherein adjusting an operating parameter of the downhole tool based on the predicted parameter comprises at least one of:
   initiating storage of a sample of the formation fluid flowing through the downhole tool based on the predicted parameter; and adjusting a rate of pumping of formation fluid into the downhole tool based on the predicted parameter.

* * * * *